(12) United States Patent
Hogan et al.

(10) Patent No.: US 9,637,513 B2
(45) Date of Patent: *May 2, 2017

(54) MATRICES AND MEDIA FOR STORAGE AND STABILIZATION OF BIOMOLECULES

(71) Applicant: GenTegra LLC, Pleasanton, CA (US)

(72) Inventors: Michael Hogan, Tucson, AZ (US); Michael Saghbini, Poway, CA (US); David Wong, San Marcos, CA (US)

(73) Assignee: GenTegra LLC, Pleasanton, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/596,925

(22) Filed: Jan. 14, 2015

(65) Prior Publication Data
US 2015/0158902 A1 Jun. 11, 2015

Related U.S. Application Data

(63) Continuation of application No. 13/590,025, filed on Aug. 20, 2012, now Pat. No. 8,951,719.

(60) Provisional application No. 61/096,747, filed on Sep. 12, 2008.

(51) Int. Cl.
| | |
|---|---|
| C09K 15/30 | (2006.01) |
| C12N 5/071 | (2010.01) |
| C12N 5/078 | (2010.01) |
| C07H 21/04 | (2006.01) |
| C07H 21/02 | (2006.01) |
| C12N 9/96 | (2006.01) |
| C12N 15/10 | (2006.01) |
| C12Q 1/68 | (2006.01) |

(52) U.S. Cl.
CPC ............ *C07H 21/02* (2013.01); *C07H 21/04* (2013.01); *C09K 15/30* (2013.01); *C12N 5/0632* (2013.01); *C12N 5/0634* (2013.01); *C12N 9/96* (2013.01); *C12N 15/10* (2013.01); *C12Q 1/6806* (2013.01); *Y10T 428/139* (2015.01); *Y10T 428/1397* (2015.01)

(58) Field of Classification Search
None
See application file for complete search history.

(56) References Cited

U.S. PATENT DOCUMENTS

| | | |
|---|---|---|
| 2,938,794 A | 5/1960 | Herman |
| 4,292,920 A | 10/1981 | Smith et al. |
| 4,643,879 A | 2/1987 | Hanaway |
| 4,684,613 A | 8/1987 | Barrere et al. |
| 4,767,716 A | 8/1988 | Sakamaki et al. |
| 4,824,641 A | 4/1989 | Williams |
| 4,891,319 A | 1/1990 | Roser |
| 4,896,024 A | 1/1990 | Morello et al. |
| 5,011,779 A | 4/1991 | Maimon |
| 5,034,506 A | 7/1991 | Summerton et al. |
| 5,096,676 A | 3/1992 | McPherson et al. |
| 5,102,804 A | 4/1992 | Fischer et al. |
| 5,120,662 A | 6/1992 | Chan et al. |
| 5,125,240 A | 6/1992 | Knippscheer et al. |
| 5,139,744 A | 8/1992 | Kowalski |
| 5,141,868 A | 8/1992 | Shanks et al. |
| 5,223,618 A | 6/1993 | Cook et al. |
| 5,355,304 A | 10/1994 | DeMoranville et al. |
| 5,366,896 A | 11/1994 | Margrey et al. |
| 5,378,825 A | 1/1995 | Cook et al. |
| 5,411,065 A | 5/1995 | Meador et al. |
| 5,411,893 A | 5/1995 | Eden et al. |
| 5,424,036 A | 6/1995 | Ushikubo |
| 5,441,698 A | 8/1995 | Norell |
| 5,445,294 A | 8/1995 | Gardner et al. |
| 5,460,057 A | 10/1995 | Ostrup |
| 5,496,562 A | 3/1996 | Burgoyne |
| 5,516,487 A | 5/1996 | Rosenthal et al. |
| 5,631,844 A | 5/1997 | Margrey |
| 5,637,508 A | 6/1997 | Kidwell et al. |
| 5,638,170 A | 6/1997 | Trinka et al. |
| 5,736,332 A | 4/1998 | Mandecki |
| 5,756,126 A | 5/1998 | Burgoyne |
| 5,800,777 A | 9/1998 | Jehan |
| 5,800,785 A | 9/1998 | Bochner |
| 5,805,456 A | 9/1998 | Higham et al. |
| 5,807,527 A | 9/1998 | Burgoyne |
| 5,841,975 A | 11/1998 | Layne et al. |
| 5,850,442 A | 12/1998 | Muftic |

(Continued)

FOREIGN PATENT DOCUMENTS

| | | |
|---|---|---|
| DE | 19716154 A1 | 10/1998 |
| EP | 0198413 A2 | 10/1986 |

(Continued)

OTHER PUBLICATIONS

Belgrader, et al. Coupled DNA Purification and PCR Amplication of STR Loci from Bloodstain Cards using a Robotic System. BioTechniques. 1995; 19:427-432.
Bever, et al. Implementation of Laboratory Automation for the Analysis of STR Loci. 8th International Symposium on Human ID. 1997.
Elliot, et al. Extraction of DNA from FTA Blood Stain Collection Cards for Construction of a Large STR National DNA Data Base. 8th International Symposium on Human ID. 1997.
European office action dated Mar. 14, 2006 for EP 02792241.8.
European office action dated May 9, 2008 for EP 02776478.6.
European office action dated May 10, 2006 for EP 02776478.6.
European office action dated May 19, 2008 for EP 05754240.9.
European office action dated Sep. 21, 2004 for EP 02776478.6.
European search report dated Jun. 16, 2011 for EP 03812020.0.
European search report dated Dec. 6, 2010 for EP 03736489.0.
Final Office Action dated Jan. 5, 2006 for U.S. Appl. No. 10/150,771.
Final Office Action dated Mar. 31, 2005 for U.S. Appl. No. 10/007,355.
Final Office Action dated Jul. 11, 2007 for U.S. Appl. No. 10/150,771.
Final Office Action dated Jul. 21, 2005 for U.S. Appl. No. 10/150,771.

(Continued)

*Primary Examiner* — David Thomas
(74) *Attorney, Agent, or Firm* — McKee, Voorhees & Sease, PLC

(57) ABSTRACT

The present invention provides compositions useful for biomolecule storage comprising a water soluble inorganic compound, a stabilizer, or a combination thereof. The present invention also provides methods of using the compositions of the invention to store biomolecules in the dry state and in solution, as well as sample carriers and kits comprising compositions of the invention.

22 Claims, 9 Drawing Sheets

(56) References Cited

U.S. PATENT DOCUMENTS

| | | | |
|---|---|---|---|
| 5,853,666 A | 12/1998 | Seaton et al. |
| 5,912,128 A | 6/1999 | Lal et al. |
| 5,916,812 A | 6/1999 | Chen et al. |
| 5,920,871 A | 7/1999 | Macri et al. |
| 5,922,617 A | 7/1999 | Wang et al. |
| 5,955,448 A | 9/1999 | Colaco et al. |
| 5,968,731 A | 10/1999 | Layne |
| 5,981,166 A | 11/1999 | Mandecki |
| 5,984,116 A | 11/1999 | Babbs |
| 5,985,214 A | 11/1999 | Stylli et al. |
| 5,985,217 A | 11/1999 | Krulevitch |
| 5,993,387 A | 11/1999 | Moore |
| 6,007,779 A | 12/1999 | Lemieux et al. |
| 6,086,824 A | 7/2000 | Fanning et al. |
| 6,098,819 A | 8/2000 | Link |
| 6,103,518 A | 8/2000 | Leighton |
| 6,108,588 A | 8/2000 | McGrady |
| 6,110,748 A | 8/2000 | Reber et al. |
| 6,127,928 A | 10/2000 | Issacman et al. |
| 6,132,685 A | 10/2000 | Kercso et al. |
| 6,156,565 A | 12/2000 | Maes et al. |
| 6,159,425 A | 12/2000 | Edwards et al. |
| 6,182,719 B1 | 2/2001 | Yahiro |
| 6,221,575 B1 | 4/2001 | Roser et al. |
| 6,245,295 B1 | 6/2001 | Chen et al. |
| 6,251,343 B1 | 6/2001 | Dubrow et al. |
| 6,260,024 B1 | 7/2001 | Shkedy |
| 6,265,219 B1 | 7/2001 | Giger et al. |
| 6,274,374 B1 | 8/2001 | Astle |
| 6,294,203 B1 | 9/2001 | Burgoyne |
| 6,313,102 B1 | 11/2001 | Colaco et al. |
| 6,325,114 B1 | 12/2001 | Bevirt et al. |
| 6,350,620 B2 | 2/2002 | Chang et al. |
| 6,358,470 B1 | 3/2002 | Higuchi |
| 6,362,737 B1 | 3/2002 | Rodgers et al. |
| 6,366,682 B1 | 4/2002 | Hoffman et al. |
| 6,372,185 B1 | 4/2002 | Shumate et al. |
| 6,395,231 B1 | 5/2002 | Kraemer et al. |
| 6,402,837 B1 | 6/2002 | Shtrahman et al. |
| 6,408,878 B2 | 6/2002 | Unger et al. |
| 6,416,719 B1 | 7/2002 | Fawcett et al. |
| 6,418,416 B1 | 7/2002 | Rosenberg et al. |
| 6,464,942 B2 | 10/2002 | Coffman et al. |
| 6,472,218 B1 | 10/2002 | Stylli et al. |
| 6,485,690 B1 | 11/2002 | Pfost et al. |
| 6,485,978 B1 | 11/2002 | Kirckof et al. |
| 6,493,724 B1 | 12/2002 | Cusack et al. |
| 6,508,984 B1 | 1/2003 | Turner et al. |
| 6,518,060 B2 | 2/2003 | Heimberg et al. |
| 6,534,015 B1 | 3/2003 | Viot et al. |
| 6,556,923 B2 | 4/2003 | Gallagher et al. |
| 6,649,386 B2 | 11/2003 | Roser |
| 6,649,403 B1 | 11/2003 | McDevitt et al. |
| 6,652,724 B2 | 11/2003 | Michael et al. |
| 6,678,577 B1 | 1/2004 | Stylli et al. |
| 6,685,884 B2 | 2/2004 | Stylli et al. |
| 6,685,940 B2 | 2/2004 | Andya et al. |
| 6,686,158 B2 | 2/2004 | Mandecki |
| 6,689,755 B1 | 2/2004 | Gabel et al. |
| 6,699,710 B1 | 3/2004 | Kononen et al. |
| 6,752,967 B2 | 6/2004 | Farina et al. |
| 6,767,748 B2 | 7/2004 | Yokokawa et al. |
| 6,811,752 B2 | 11/2004 | Barbera-Guillem |
| 6,943,035 B1 | 9/2005 | Davies et al. |
| 7,142,987 B2 | 11/2006 | Eggers |
| 7,225,082 B1 | 5/2007 | Natan et al. |
| 7,276,208 B2 | 10/2007 | Sevigny et al. |
| 7,312,085 B2 | 12/2007 | Chou et al. |
| 7,354,774 B2 | 4/2008 | Hughes et al. |
| 7,584,240 B2 | 9/2009 | Eggers et al. |
| 7,589,184 B2 | 9/2009 | Hogan et al. |
| 7,718,442 B2 | 5/2010 | Davis et al. |
| 8,283,165 B2 * | 10/2012 | Hogan ............... C12N 9/96 435/374 |
| 8,951,719 B2 * | 2/2015 | Hogan ............... C12N 9/96 252/397 |
| 2002/0006673 A1 | 1/2002 | Mandecki |
| 2002/0176803 A1 | 11/2002 | Hamel et al. |
| 2003/0000597 A1 | 1/2003 | Ganz et al. |
| 2003/0027788 A1 | 2/2003 | Singh et al. |
| 2003/0044991 A1 | 3/2003 | Haslam et al. |
| 2003/0046114 A1 | 3/2003 | Davies |
| 2003/0087425 A1 | 5/2003 | Eggers |
| 2003/0087455 A1 | 5/2003 | Eggers et al. |
| 2003/0129089 A1 | 7/2003 | Arnold et al. |
| 2003/0129755 A1 | 7/2003 | Sadler et al. |
| 2003/0161761 A1 | 8/2003 | Williams et al. |
| 2003/0215361 A1 | 11/2003 | Jang |
| 2003/0215369 A1 | 11/2003 | Eggers et al. |
| 2004/0014228 A1 | 1/2004 | Brignac et al. |
| 2004/0053318 A1 | 3/2004 | McWilliams et al. |
| 2004/0059107 A1 | 3/2004 | Malfroy-Camine et al. |
| 2004/0098204 A1 | 5/2004 | Milosavljevic et al. |
| 2004/0101966 A1 | 5/2004 | Davis et al. |
| 2004/0133936 A1 * | 7/2004 | Rossiter ............... A61K 38/47 800/278 |
| 2004/0142893 A1 | 7/2004 | Ikeda et al. |
| 2004/0219533 A1 | 11/2004 | Davis et al. |
| 2004/0229038 A1 | 11/2004 | Cooper et al. |
| 2005/0026181 A1 | 2/2005 | Davis et al. |
| 2005/0074478 A1 | 4/2005 | Ofstead et al. |
| 2006/0014177 A1 | 1/2006 | Hogan et al. |
| 2006/0099567 A1 | 5/2006 | Muller-Cohn et al. |
| 2008/0050793 A1 | 2/2008 | Durance et al. |
| 2009/0105465 A1 * | 4/2009 | Arunakumari ... A61K 39/39525 530/416 |
| 2009/0212260 A1 | 8/2009 | Paknikar |
| 2009/0311269 A1 | 12/2009 | Allen et al. |
| 2010/0062418 A1 | 3/2010 | Mach et al. |
| 2010/0087352 A1 | 4/2010 | Mason |
| 2010/0178210 A1 | 7/2010 | Hogan et al. |
| 2010/0209957 A1 | 8/2010 | Hogan et al. |
| 2010/0218623 A1 | 9/2010 | Eggers et al. |
| 2012/0100522 A1 | 4/2012 | Saghbini et al. |

FOREIGN PATENT DOCUMENTS

| | | |
|---|---|---|
| EP | 0198413 A3 | 12/1987 |
| EP | 1155742 A2 | 11/2001 |
| EP | 1155742 A3 | 1/2002 |
| EP | 1179585 A2 | 2/2002 |
| EP | 1179585 A3 | 3/2002 |
| EP | 1965326 A2 | 9/2008 |
| EP | 1965326 A3 | 12/2008 |
| GB | 2369086 A | 2/2002 |
| GB | 2380259 A | 4/2003 |
| JP | 1078388 A | 3/1998 |
| JP | 2002125656 A | 5/2002 |
| JP | 2008275648 | 11/2008 |
| WO | 8700196 A1 | 1/1987 |
| WO | 9411388 A1 | 5/1994 |
| WO | 9611406 A1 | 4/1996 |
| WO | 9640077 A2 | 12/1996 |
| WO | 9640077 A3 | 1/1997 |
| WO | 9810787 A2 | 3/1998 |
| WO | 9810792 A1 | 3/1998 |
| WO | 9813684 A1 | 4/1998 |
| WO | 9820019 A1 | 5/1998 |
| WO | 9810787 A3 | 7/1998 |
| WO | 9829736 A1 | 7/1998 |
| WO | 9847516 A1 | 10/1998 |
| WO | 9934214 A1 | 7/1999 |
| WO | 9938962 A2 | 8/1999 |
| WO | 9939716 A1 | 8/1999 |
| WO | 9944062 A1 | 9/1999 |
| WO | 9938962 A3 | 10/1999 |
| WO | 0009150 A2 | 2/2000 |
| WO | 0023478 A1 | 4/2000 |
| WO | 0009150 A3 | 5/2000 |
| WO | 0035472 A2 | 6/2000 |
| WO | 0042030 A1 | 7/2000 |
| WO | 0048735 A2 | 8/2000 |
| WO | 0049382 A2 | 8/2000 |

(56) References Cited

FOREIGN PATENT DOCUMENTS

| WO | 0035472 A3 | 11/2000 |
|---|---|---|
| WO | 0066360 A1 | 11/2000 |
| WO | 0048735 A3 | 12/2000 |
| WO | 0049382 A3 | 1/2001 |
| WO | 0112327 A1 | 2/2001 |
| WO | 0118239 A1 | 3/2001 |
| WO | 0131317 A1 | 5/2001 |
| WO | 0131333 A1 | 5/2001 |
| WO | 0142796 A1 | 6/2001 |
| WO | 0186410 A1 | 11/2001 |
| WO | 0194016 A1 | 12/2001 |
| WO | 0246719 A3 | 2/2002 |
| WO | 0230561 A2 | 4/2002 |
| WO | 0246719 A2 | 6/2002 |
| WO | 03020924 A2 | 3/2003 |
| WO | 03022435 A2 | 3/2003 |
| WO | 03031929 A2 | 4/2003 |
| WO | 0230561 A3 | 5/2003 |
| WO | 03039749 A2 | 5/2003 |
| WO | 03049861 A1 | 6/2003 |
| WO | 03020924 A3 | 7/2003 |
| WO | 03031929 A3 | 8/2003 |
| WO | 03022435 A3 | 12/2003 |
| WO | 03039749 A3 | 2/2004 |
| WO | 2004033470 A2 | 4/2004 |
| WO | 2004033470 A3 | 9/2004 |
| WO | 2005116081 A2 | 12/2005 |
| WO | 2005116081 A3 | 7/2006 |

OTHER PUBLICATIONS

Final Office Action dated Sep. 24, 2008 for U.S. Appl. No. 10/150,771.
Final Office Action dated Sep. 25, 2009 for U.S. Appl. No. 10/150,771.
Final Office Action dated Oct. 8, 2012 for U.S. Appl. No. 12/732,154.
Final Office Action dated Dec. 8, 2005 for U.S. Appl. No. 10/007,355.
Final Office Action dated Dec. 16, 2009 for U.S. Appl. No. 10/007,355.
Hansen, et al. Sample Archiving of Bacterial and Plasmid DNAs for Future Use. Focus. 1998; 20(3):72-74.
International search report dated Feb. 17, 2010 for PCT/US2009/048187.
International search report dated Feb. 26, 2004 for PCT/US2002/036101.
International search report dated Mar. 19, 2003 for PCT/US2002/036099.
International search report dated Apr. 13, 2004 for PCT/US2003/028437.
International search report dated May 5, 2005 for PCT/US2003/032611.
International search report dated May 18, 2006 for PCT/US2005/018092.
International search report dated May 31, 2010 for PCT/US2009/056869.
International search report dated Jul. 30, 2003 for PCT/US2003/012852.
International search report dated Aug. 22, 2003 for PCT/US2003/012850.
International search report dated Oct. 12, 2003 for PCT/US2002/036108.
International search report and written opinion dated Aug. 9, 2011 for PCT/US2011/031477.
Office Action dated Jan. 31, 2006 for U.S. Appl. No. 10/252,352.
Office Action dated Feb. 1, 2007 for U.S. Appl. No. 10/150,771.
Office Action dated Feb. 2, 2009 for U.S. Appl. No. 10/252,352.
Office Action dated Feb. 12, 2008 for U.S. Appl. No. 10/150,771.
Office Action dated Feb. 15, 2006 for U.S. Appl. No. 10/005,415.
Office Action dated Feb. 26, 2008 for U.S. Appl. No. 11/137,806.
Office Action dated Mar. 4, 2008 for U.S. Appl. No. 10/2005,415.
Office Action dated Mar. 22, 2006 for U.S. Appl. No. 10/150,770.
Office Action dated Mar. 22, 2006 for U.S. Appl. No. 10/302,647.
Office Action dated Mar. 24, 2004 for U.S. Appl. No. 10/252,352.
Office Action dated Apr. 2, 2009 for U.S. Appl. No. 10/302,647.
Office Action dated Apr. 4, 2007 for U.S. Appl. No. 10/150,770.
Office Action dated Apr. 5, 2005 for U.S. Appl. No. 10/252,352.
Office Action dated Apr. 23, 2009 for U.S. Appl. No. 10/007,355.
Office Action dated Jun. 13, 2005 for U.S. Appl. No. 10/005,415.
Office Action dated Jun. 25, 2008 for U.S. Appl. No. 10/302,647.
Office Action dated Jun. 30, 2005 for U.S. Appl. No. 10/005,529.
Office Action dated Aug. 28, 2006 for U.S. Appl. No. 10/005,415.
Office Action dated Sep. 2, 2008 for U.S. Appl. No. 10/005,415.
Office Action dated Sep. 6, 2006 for U.S. Appl. No. 10/302,647.
Office Action dated Sep. 8, 2006 for U.S. Appl. No. 10/150,770.
Office Action dated Sep. 12, 2007 for U.S. Appl. No. 10/005,415.
Office Action dated Sep. 13, 2004 for U.S. Appl. No. 10/007,355.
Office Action dated Sep. 16, 2004 for U.S. Appl. No. 10/252,352.
Office Action dated Sep. 25, 2008 for U.S. Appl. No. 11/137,806.
Office Action dated Oct. 3, 2007 for U.S. Appl. No. 10/302,647.
Office Action dated Oct. 14, 2004 for U.S. Appl. No. 10/150,771.
Office Action dated Oct. 17, 2007 for U.S. Appl. No. 10/150,770.
Office Action dated Nov. 4, 2004 for U.S. Appl. No. 10/005,529.
Perry-Okeefe, et al. Peptide nucleic acid pre-gel hybridization: an alternative to southern hybridization. Proc Natl Acad Sci U S A. Dec. 10, 1996;93(25):14670-5.
Zhang, et al., Single gene retrieval from thermally degraded DNA, J. Biosci. Dec. 2005, vol. 30, pp. 599-604.
European search report and opinion dated Dec. 12, 2011 for EP 9011209.5.
Japanese office action dated Apr. 26, 2011 for JP Application No. 2009-158280.
Canadian office action dated Mar. 5, 2012 for CA Application No. 2,567,720.
Harty, et al. Collection of buccal cell DNA using treated cards. Cancer Epidemiol Biomarkers Prev. May 2000;9(5):501-6.
Nokes, et al. A comparison of oral fluid and serum for the detection of rubella-specific antibodies in a community study in Addis Ababa, Ethiopia. Trop Med Int Health. Apr. 1998;3(4):258-67.
Nokes, et al. An evaluation of oral-fluid collection devices for the determination of rubella antibody status in a rural Ethiopian community. Trans R Soc Trop Med Hyg. Nov.-Dec. 1998;92(6):679-85.
Office Action dated Mar. 14, 2012 for U.S. Appl. No. 12/499,031.
Ware, et al. Comparison of sponging and excising as sampling procedures for microbiological analysis of fresh beef-carcass tissue. J Food Prot. Nov. 1999;62(11):1255-9.
Zhong, et al. Comparison of IsoCode STIX and FTA Gene Guard collection matrices as whole-blood storage and processing devices for diagnosis of malaria by PCR. J Clin Microbiol. Mar. 2001;39(3):1195-6.

\* cited by examiner

Red = Room Temp
Blue = 37C
Green = 56 C
Black = Control

Figure 4

|  |  | % call rate | % concordance to control |
|---|---|---|---|
| Illumina 1M | Boric acid | 99.75 | 99.9988 |
| | Boric acid + His | 99.76 | 99.9995 |
| Affy 6.0 | Boric acid | 99.42 | 99.729 |
| | Boric acid + His | 99.63 | 99.871 |

MATRICES AND MEDIA FOR STORAGE AND STABILIZATION OF BIOMOLECULES

CROSS-REFERENCE TO RELATED APPLICATIONS

This is a Continuation Application of U.S. application Ser. No. 13/590,025, filed on Aug. 20, 2012, which claims priority from U.S. Provisional Application No. 61/096,747, filed on Sep. 12, 2008, the contents of which are expressly incorporated herein by reference.

BACKGROUND OF THE INVENTION

In many applications, such as pharmaceutical and medical research, law enforcement, and military identification, it is often desirable to store and to have access to numerous biological samples. Conventional biorepositories or other sample storage facilities utilize liquid or low temperature cryogenic systems for sample storage. These liquid and cryogenic systems are expensive both to create and to maintain, and current technology generally presents system operators with complicated and labor intensive maintenance and administrative responsibilities. In addition, these systems do not address work flow concerns that arise when large numbers of samples are being processed simultaneously. Under such conditions, samples can be left at ambient temperature for long periods of time, resulting in sample degradation.

Related to the issue of work flow, it is becoming increasingly important to ship samples that are collected in the field or elsewhere so that the samples can be analyzed and/or stored at a remote location. However, shipping samples on dry ice is expensive and hazardous and standard modes of shipping, like those employed by carriers such as FedEx, can subject samples to large temperature fluctuations, including high temperatures that can denature or degrade biomolecules present in biological samples. For example, FedEx cautions that temperatures in carrier vehicles can reach 140° F. (60° C.) in closed, parked carrier vehicles during the summer in southern climates. Similarly, for worldwide transportation applications, the U.S. military assumes a worst case scenario where samples are exposed to temperatures as high as 160° F. (71° C.).

There is a need in the field to develop additional biomolecule storage materials and systems.

SUMMARY OF THE INVENTION

The present invention is based, in part, on the discovery that certain compounds, especially water soluble inorganic compounds and compounds that function as singlet oxygen quenchers, are useful for the stabilization and/or storage of biomolecules in the dry state, including at elevated temperatures. The invention is also based, in part, on the discovery that certain combinations of compounds stabilize biomolecules, including RNA, in aqueous solution. Accordingly, the present invention provides compositions, devices and methods useful for stabilization and storage of biomolecules.

In one aspect, the invention provides compositions useful for biomolecule storage and/or stabilization. In certain embodiments, the composition is a matrix (e.g., a solid state matrix) comprising a water soluble inorganic compound, a stabilizer (e.g., a small molecule stabilizer), or a combination thereof. In other embodiments, the composition is a medium (e.g., an aqueous medium) comprising a water soluble inorganic compound, a stabilizer (e.g., a small molecule stabilizer), or a combination thereof. In still other embodiments, the composition is a matrix (e.g., a solid state matrix) or a medium (e.g., an aqueous medium) comprising at least three components selected from the list consisting of an inorganic compound, a singlet oxygen quencher, a hydroxyl radical scavenger, a hydroperoxide removing agent, a reducing agent, a metal chelator, a detergent, and a plasticizer. In certain embodiments, the matrix or medium further comprises a plasticizer. In certain embodiments, the matrix or medium further comprises an RNase inhibitor. In certain embodiments, the matrix or medium further comprises biomolecules (e.g., nucleic acids, such as DNA or RNA). For example, the matrix or medium can comprise a sample, such as a biological sample, that contains biomolecules.

In another aspect, the invention provides a sample carrier useful for storing biomolecules. In certain embodiments, the sample carrier comprises a container and a sample node, wherein the sample node is a composition disclosed herein (e.g., a matrix or a medium disclosed herein). The container can, for example, support the sample node. In certain embodiments, the sample carrier comprises a plurality of containers and a plurality of discrete sample nodes. Each of the plurality of sample nodes, for example, can be individually supported by a single container. In certain embodiments, the sample carrier further comprises biomolecules. For example, the sample carrier can comprise one or more samples, such as biological samples, that contain biomolecules. The biomolecules can be, for example, stored in a sample node (e.g., mixed with a matrix or medium disclosed herein). In certain embodiments, the sample carrier comprises an identifying indicia. In certain embodiments, the container or sample node comprises an identifying indicia.

In another aspect, the invention provides kits comprising a composition disclosed herein (e.g., a matrix or a medium disclosed herein) and an instruction for using the composition for storage and/or stabilization (e.g., dry-state storage or stabilization in an aqueous medium) of biomolecules. In certain embodiments, the kit includes a container that contains the composition. In certain embodiments, the kit includes a sample carrier disclosed herein.

In another aspect, the invention provides methods of storing and/or stabilizing biomolecules. In certain embodiments, the methods comprise mixing a sample that contains biomolecules, such as a biological sample, with a composition disclosed herein (e.g., a matrix or a medium disclosed herein) to form a mixture, and drying down the mixture. In certain embodiments, the sample is a liquid sample, such as a bodily fluid, a cellular lysate, or a tissue homogenate. In certain embodiments, the sample is carried by a solid support, such as a cotton swab, a filter paper, or a sponge. In certain related embodiments, mixing comprises rinsing a solid support that carries the sample with a medium disclosed herein.

Additional aspects and details of the invention will be evident from the detailed description that follows.

BRIEF DESCRIPTION OF THE FIGURES

FIG. 4 shows microarray data for DNA recovered from 1 μg DNA samples following dry-state storage at room temperature, in a matrix composed of boric acid or boric acid and histidine.

DETAILED DESCRIPTION OF THE INVENTION

Figure 1:
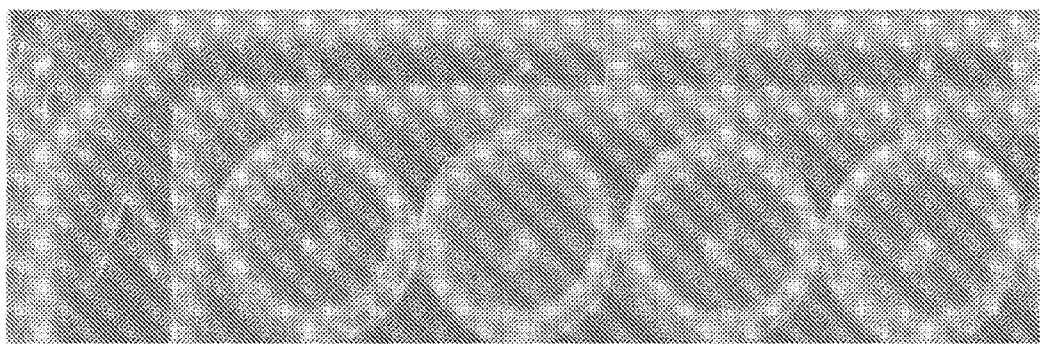
FIG. 1 is an image of a sample carrier that has a plurality of containers and a plurality of discrete sample nodes. In this embodiment, the containers are the wells of a multi-well plate. Each of the containers shown supports a single discrete sample node. Each discrete sample node consists of a solid state storage matrix formed by evaporation of a storage medium containing boric acid and DNA.

As used herein, the following terms shall have the following meanings.

The term "biomolecules" is expressly intended to include short and long biopolymers including, but not limited to, such polymeric molecules as DNA, RNA, proteins, immunoglobulins, and carbohydrates, whether naturally existing or synthesized and with or without modifications, such as modified amino acids or nucleotides. Thus, for example, the term includes both short, oligomeric nucleic acid molecules (e.g., less than 50 bases in length), long nucleic acid molecules (e.g., greater than 50 kB in length), and any length in between. The term similarly encompasses both short peptide sequences (e.g., less than 10 amino acids), long polypeptide sequences (e.g., greater than 1000 amino acids in length), and any length in between. In addition, the term "biomolecules" is expressly intended to include small molecules found in biological samples, such as lipids, coenzymes, metabolites, and pharmaceutical agents and their metabolites.

The term "protein" as used herein is used interchangeably with the term "polypeptide."

The term "nucleic acid," "oligonucleotide" and "polynucleotide" are used interchangeably and encompass DNA, RNA, cDNA, whether single stranded or double stranded, as well as chemical modifications thereof and artificial nucleic acids (e.g., PNA, LNA, etc.).

Compositions

The present invention is based, in part, on the discovery that certain compounds, especially water soluble inorganic compounds and compounds that function as singlet oxygen quenchers, are useful for the stabilization and/or storage of biomolecules in the dry state, including at elevated temperatures. The invention is also based, in part, on the discovery that certain combinations of compounds stabilize biomolecules, including RNA, in aqueous solution.

Accordingly, in one aspect, the present invention provides compositions useful for storing and/or stabilizing biomolecules. In certain embodiments, the compositions comprise an inorganic compound, wherein the inorganic compound is water soluble.

As used herein, an "inorganic compound" is a compound having a molecular formula that does not include carbon. In certain embodiments, the inorganic compound is an acid (i.e., a compound that, when dissolved in water, gives rise to a solution having a pH less than 7.0). In certain embodiments, the inorganic compound is a base (i.e., a compound that, when dissolved in water, gives rise to a solution having a pH greater than 7.0). In other embodiments, the inorganic compound is not a base (e.g., the inorganic compound is not a Lewis base). In still other embodiments, the inorganic compound is a salt.

In certain embodiments, the inorganic compound is a metal chelator. As used herein, a "metal chelator" is a compound that forms two or more bonds with a single metal ion. In certain embodiments, the inorganic compound chelates at least one type of metal ion selected from the group consisting of magnesium ions, chromium ions, manganese ions, iron ions, cobalt ions, nickel ions, copper ions, zinc ions, lead ions, or any combination thereof. In certain embodiments, the inorganic compound chelates at least one type of metal ion and inhibits metal-dependent reactions between such ions and biomolecules present in the composition. In certain embodiments, the inorganic compound chelates at least one type of metal ion and prevents such ions from degrading biomolecules present in the composition. In preferred embodiments, the inorganic compound chelates magnesium ions and/or manganese ions and inhibits metal-dependant reactions between such ions and biomolecules present in the composition. In other preferred embodiments, the inorganic compound chelates magnesium ions and/or manganese ions and prevents such ions from degrading biomolecules present in the composition.

In certain embodiments, the inorganic compound is a microcidal agent. As used herein, a "microcidal agent" is any compound that slows or stops the growth of a microorganism. In certain embodiments, the inorganic compound kills one or more microbial organism, such as a bacterium, protist, and/or fungus. In certain embodiments, the inorganic compound inhibits the growth of one or more microbial organism, such as a bacterium, protist, virus, or fungus.

In certain embodiments, the inorganic compound is capable of absorbing or sequestering water molecules, thereby preventing hydrolysis of biomolecules. In certain embodiments, the inorganic compound, when equilibrated with atmospheric humidity of 50%, is hydrated to about 70%, 60%, 50%, 45%, 40%, 38%, 36%, 35%, 34%, 33%, 32%, 31%, 30%, or less by mass.

In certain embodiments, the inorganic compound concentrates upon drying and forms a crystalline or paracrystalline structure. In certain embodiments, the inorganic compound does not form a glass structure upon drying. As used herein, the term "glass structure" refers to a solid-state structure in which the molecules comprising the glass structure display only short-range order, rather than extended-range crystalline order with respect to one another. In certain embodiments, the inorganic compound is capable of co-localization with biomolecules. For example, in certain embodiments, the inorganic compound concentrates upon drying and forms a crystalline or paracrystalline state in direct contact with biomolecules.

In certain embodiments, the inorganic compound is inert with respect to one or more types of biomolecules. As used herein in this context, "inert" means that the inorganic compound either does not bind to one or more types of biomolecules or binds reversibly such that the biomolecules are not degraded as a result of such binding. In preferred embodiments, the inorganic compound is inert with respect to nucleic acids, proteins, carbohydrates, lipids, coenzymes, metabolites, pharmaceutical agents, metabolites of pharmaceutical agents, or any combination thereof.

In certain embodiments, the inorganic compound is inert with respect to one or more downstream methods that may be used to analyze biomolecules that have been stored in and/or stabilized by a composition of the invention. The term "inert," as used herein in this context, means that the presence of inorganic compound in a sample does not reduce the rate of the method by more than 50% and does significantly reduce the fidelity of the method. In certain embodiments, the inorganic compound is inert with respect to a method selected from the group consisting of nucleic acid transcription and/or amplification (e.g., reverse transcription, PCR, real time PCR, etc.), endonuclease digestion (e.g., reactions involving type II endonucleases, such as EcoRI, BamBI, Hindiii, Noti, Smai, Bglii, etc.), cloning techniques (e.g., ligation), protein digestion (e.g., reactions involving proteinases such as proteinase K, trypsin, chymotrypsin, savinase, etc.), microarray analysis (e.g., of nucleic acids or proteins), immunoassays (e.g., immunoprecipitation, ELISA, etc.), mass spectroscopy, or any combination thereof. In certain embodiments, the inorganic compound is inert upon dilution (e.g., dilution by a factor of 2, 3, 4, 5, 6, 7, 8, 9, 10, 15, 20, or more). In other embodiments, the inorganic compound is inert in undiluted form. In certain embodiments, the inorganic compound is inert with respect to one or more such methods when present in the reaction at concentrations of 0.075 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 2.0 mg/ml, 5.0 mg/ml, 10.0 mg/ml, or greater.

As used herein in this context, "water soluble" means that the inorganic compound has a solubility in water, at 25° C., of 1.0 mg/ml or greater. In certain embodiments, the inorganic compound has a solubility in water, at 25° C., of at least 1.5 mg/ml, 2.0 mg/ml, 3.0 mg/ml, 4.0 mg/ml, 5.0 mg/ml, 7.5 mg/ml, 10 mg/ml, 15 mg/ml, 20 mg/ml, 25 mg/ml, 30 mg/ml, 35 mg/ml, 40 mg/ml, 50 mg/ml, 60 mg/ml, 70 mg/ml, 80 mg/ml, 90 mg/ml, 100 mg/ml, 125 mg/ml, 150 mg/ml, 200 mg/ml, or greater. In certain embodiments, the inorganic compound can be easily solubilized in water. For example, in certain embodiments, the inorganic compound can be solubilized in water, at 25° C., in 75, 60, 50, 40, 30, 25, 20, 15, 10, 9, 8, 7, 6, 5, 4, 3, 2, or fewer minutes. In other embodiments, the inorganic compound can be solubilized in water, at 25° C., in 7, 6, 5, 4, 3, 2, 1.5, or fewer hours. In certain embodiments, the inorganic compound can be solubilized in water, at 25° C., with or without the use of agitation (e.g., pipetting, shaking, or vortexing).

In certain embodiments, the inorganic compound has a molecular formula that comprises an element from the first (e.g., VA), third (e.g., IIIA or IIIB), fifth (e.g., VA or VB), sixth (e.g., VIA), or seventh (e.g., VIIA) Group of the Periodic Table of Elements, or a combination thereof. For example, in certain embodiments, the inorganic compound has a molecular formula that comprises hydrogen, sodium, potassium, boron, aluminum, phosphorus, vanadium, oxygen, sulfur, chloride, or a combination thereof. In certain embodiments, the inorganic compound has a molecular formula that comprises an element from at least the third (e.g., IIIA or IIIB) or fifth (e.g., VA or VB) Group of the Periodic table of elements. In certain embodiments, the inorganic compound has a molecular formula that comprises boron, aluminum, phosphorus, or vanadium. In other embodiments, the inorganic compound has a molecular formula that does not comprise an element selected from the group consisting of boron, aluminum, phosphorus, vanadium, or a combination thereof.

In certain embodiments, the inorganic compound is boric acid or a corresponding salt of boric acid (e.g., borax). In certain embodiments, the inorganic compound is phosphoric acid or a corresponding salt of phosphoric acid (e.g., $Na_3PO_4$, $Na_2HPO_4$, $NaH_2PO_4$, $K_3PO_4$, $K_2HPO_4$, $KH_2PO_4$). In certain embodiments, the inorganic compound is a vanadate salt (e.g., $Na_3VO_4$, $K_3VO_4$). In certain embodiments, the inorganic compound is an aluminum salt (e.g., an alum, such as potassium alum ($KAl(SO_4)_2.12H_2O$), soda alum ($Na_2SO_4Al_2(SO_4)_3.24H_2O$), or ammonium alum ($NH_4Al(SO_4)_2.12H_2O$)). In certain embodiments, the inorganic compound is sodium chloride or potassium chloride. In certain embodiments, the inorganic compound is a combination selected from the group consisting of boric acid, a corresponding salt of boric acid (e.g., borax), phosphoric acid, a corresponding salt of phosphoric acid (e.g., $Na_3PO_4$, $Na_2HPO_4$, $NaH_2PO_4$, $K_3PO_4$, $K_2HPO_4$, $KH_2PO_4$), a vanadate salt (e.g., $Na_3VO_4$, $K_3VO_4$), an aluminum salt (e.g., an alum, such as potassium alum ($KAl(SO_4)_2.12H_2O$), soda alum ($Na_2SO_4Al_2(SO_4)_3.24H_2O$), or ammonium alum ($NH_4Al(SO_4)_2.12H_2O$)), sodium chloride, and potassium chloride.

In certain embodiments, the inorganic compound is neither boric acid nor a corresponding salt of boric acid (e.g., borax). In certain embodiments, the inorganic compound is neither phosphoric acid nor a corresponding salt of phosphoric acid (e.g., $Na_3PO_4$, $Na_2HPO_4$, $NaH_2PO_4$, $K_3PO_4$, $K_2HPO_4$, $KH_2PO_4$). In certain embodiments, the inorganic compound is not a vanadate salt (e.g., $Na_3VO_4$, $K_3VO_4$). In certain embodiments, the inorganic compound is not an aluminum salt (e.g., an alum, such as potassium alum (i.e., $KAl(SO_4)_2.12H_2O$), soda alum (i.e., $Na_2SO_4Al_2(SO_4)_3.24H_2O$), or ammonium alum (i.e., $NH_4Al(SO_4)_2.12H_2O$)). In certain embodiments, the inorganic compound is not sodium chloride. In certain embodiments, the inorganic compound is not potassium chloride.

In certain embodiments, the inorganic compound is not an inorganic mineral. As used herein, an "inorganic mineral" is an inorganic compound that is not soluble in water at 25° C. Examples of inorganic minerals include hydroxylapetite, $Ca_{10}(PO_4)_6(OH)_2$, and various clays, such as kaolin (i.e., $Al_2O_3.2SiO_2.2H_2O$) and montmorillonite (i.e., $Na_{0.2}Ca_{0.1}Al_2Si_4O_{10}(OH)_2(H_2O)_{10}$).

In certain embodiments, the inorganic compound has a molecular formula that does not include magnesium, chromium, manganese, iron, cobalt, nickel, copper, zinc, or lead.

In certain embodiments, the inorganic compound (or mixture of inorganic compounds) is the principal component of the composition. As used herein, the "principal component" of a composition is a single chemical compound (or specific set of compounds) present in greatest abundance, by weight, in the composition. In certain embodiments, the inorganic compound (or mixture of inorganic compounds) constitutes at least 5%, 10%, 15%, 20%, 25%, 30%, 35%, 40%, 45%, 50%, or more of the composition. In other embodiments, the inorganic compound (or mixture of inorganic compounds) is the principal non-water component of the composition. In certain embodiments, the inorganic compound (or mixture of inorganic compounds) constitutes at least 5%, 10%, 15%, 20%, 25%, 30%, 35%, 40%, 45%, 50%, or more of the non-water portion of the composition.

In certain embodiments, the inorganic compound (or mixture of inorganic compounds) is part of an aqueous medium of the invention and is present in a concentration of about 0.5 mg/ml to about 200 mg/ml, about 1.0 mg/ml to about 150.0 mg/ml, about 1.5 mg/ml to about 100.0 mg/ml, about 2.0 mg/ml to about 50.0 mg/ml, about 2.5 mg/ml to about 25.0 mg/ml, or about 3.0 mg/ml to about 10.0 mg/ml.

In certain embodiments, the inorganic compound (or mixture of inorganic compounds) is part of an aqueous solution of the invention and is present in a concentration of about 0.1 mg/ml to about 10 mg/ml, about 0.2 mg/ml to about 8 mg/ml, about 0.3 mg/ml to about 6 mg/ml, about 0.4 mg/ml to about 4 mg/ml, about 0.5 mg/ml to about 2 mg/ml, or about 0.6 mg/ml to about 1 mg/ml. In certain embodiments, the inorganic compound (or mixture of inorganic compounds) is part of an aqueous solution of the invention and is present in a concentration of about 5.0 mg/ml to about 150.0 mg/ml, about 10.0 mg/ml to about 125.0 mg/ml, about 20.0 mg/ml to about 100.0 mg/ml, or about 25.0 mg/ml to about 75.0 mg/ml.

In certain embodiments, the inorganic compound is part of an aqueous medium of the invention and is present in a concentration of about 5 mM to about 500 mM, about 6 mM to about 450 mM, about 7 mM to about 400 mM, about 8 mM to about 350 mM, about 9 mM to about 300 mM, about 10 mM to about 250 mM, about 10 mM to about 200 mM, about 10 mM to about 150 mM, about 15 mM to about 140 mM, about 20 mM to about 130 mM, about 25 mM to about 120 mM, about 30 mM to about 110 mM, about 35 mM to about 105 mM, or about 40 mM to about 100 mM. In certain embodiments, the inorganic compound is part of an aqueous medium of the invention and is present in a concentration of about 1 mM to about 100 mM, about 2 mM to about 80 mM, about 3 mM to about 60 mM, about 4 mM to about 40 mM, about 5 mM to about 30 mM, about 6 mM to about 25 mM, about 7 mM to about 20 mM, or about 8 mM to about 15 mM.

In certain embodiments, compositions of the invention further comprise a stabilizer. For example, in certain embodiments, the compositions comprise an inorganic compound and a stabilizer. The inorganic compound can be as described above. As used herein, a "stabilizer" is any agent capable of protecting at least one type of biomolecule from damage during storage. In certain embodiments, the at least one type of biomolecule protected by the stabilizer is DNA, protein, carbohydrates, lipids, pharmaceutical agent or metabolite thereof, or any combination thereof. In certain embodiments, the stabilizer is capable of inhibiting undesirable contact between biomolecules and various contaminants or potential sources of degradation, including but not limited to oxygen (e.g., reactive oxygen species, such as singlet oxygen, hydroxyl radicals, superoxide anions, etc.), free water, enzymes, metal ions, or other reactive chemical species.

In certain embodiments, the stabilizer concentrates upon drying and forms a crystalline or paracrystalline structure. In certain embodiments, the stabilizer does not form a glass structure upon drying. In certain embodiments, the stabilizer is capable of co-localizing with biomolecules. For example, in certain embodiments, the stabilizer concentrates upon drying and forms a crystalline or paracrystalline state in direct contact with biomolecules. The co-localization of stabilizers and biomolecules can provide additional stabilization of the biomolecule.

In certain embodiments, the stabilizer is a small molecule stabilizer. In certain embodiments, the stabilizer is selected from the group consisting of singlet oxygen quenchers, hydroxyl radical scavengers, hydroperoxide removing agents, reducing agents, metal chelators, detergents, chaotropes, and combinations thereof. Examples of singlet oxygen quenchers include, but are not limited to, alkyl imidazoles (e.g., histidine, L-carnosine, histamine, imidazole 4-acetic acid), indoles (e.g., tryptophan and derivatives thereof, such as N-acetyl-5-methoxytryptamine, N-acetylserotonin, 6-methoxy-1,2,3,4-tetrahydro-beta-carboline), sulfur-containing amino acids (e.g., methionine, ethionine, djenkolic acid, lanthionine, N-formyl methionine, felinine, S-allyl cysteine, S-aminoethyl-L-cysteine), phenolic compounds (e.g., tyrosine and derivatives thereof), aromatic acids (e.g., ascorbate, salicylic acid, and derivatives thereof), azide (e.g., sodium azide), tocopherol and related vitamin E derivatives, and carotene and related vitamin A derivatives. Examples of hydroxyl radical scavengers include, but are not limited to azide, dimethyl sulfoxide, histidine, mannitol, sucrose, glucose, salicylate, and L-cysteine. Examples of hydroperoxide removing agents include, but are not limited to catalase, pyruvate, glutathione, and glutathione peroxidases. Examples of reducing agents include, but are not limited to, cysteine and mercaptoethylene. Examples of metal chelators include, but are not limited to, EDTA, EGTA, o-phenanthroline, and citrate. Examples of detergents include, but are not limited to, SDS and sodium lauroyl sarcosyl. Examples of chaotropes include, but are not limited to guanidinium hydrochloride, isothiocyanate, urea, and formamide.

In certain embodiments, the stabilizer comprises a singlet oxygen quencher (e.g., an alkyl imidazole, an indole, or a sulfur-containing amino acid). In certain embodiments, the stabilizer comprises two or more singlet oxygen quenchers (e.g., selected from the group consisting of an alkyl imidazole, an indole, and a sulfur-containing amino acid). In certain embodiments, the stabilizer comprises a singlet oxygen quencher and a hydroxyl radical scavenger, a hydroperoxide removing agent, a metal chelator, or any combination thereof. In certain embodiments, the stabilizer comprises a hydroxyl radical scavenger. In certain embodiments, the stabilizer comprises a hydroperoxide removing agent. In certain embodiments, the stabilizer comprises a metal chelator. In certain embodiments, the stabilizer comprises two or more metal chelators. In certain embodiments, the stabilizer comprises a hydroxyl radical scavenger, a hydroperoxide removing agent, a metal chelator, or any combination thereof (e.g., a hydroxyl radical scavenger and a hydroperoxide removing agent; a hydroxyl radical scavenger and a metal chelator; a hydroperoxide removing agent and a metal chelator; a hydroxyl radical scavenger, a hydroperoxide removing agent, and a metal chelator).

In certain embodiments, the stabilizer does not comprise EDTA, EGTA, or the combination of EDTA and EGTA. In certain embodiments, the stabilizer does not comprise SDS. In certain embodiments, the stabilizer does not comprise cysteine, mercaptoethylene, or the combination of cysteine and mercaptoethylene.

In certain embodiments, the ratio of inorganic compounds to stabilizers in the composition is about 20:1 to about 1:2, about 15:1 to about 1:1.5, about 12:1 to about 1:1, about 10:1 to about 1.5:1, about 8:1 to about 2:1, or about 5:1 to about 2.5:1 by weight. In other embodiments, the ratio of inorganic compounds to stabilizers is about 5:1 to about 1:5, about 4:1 to about 1:4, about 3:1 to about 1:3, about 2:1 to about 1:2, or about 1:1. In other embodiments, the ratio of inorganic compounds to stabilizers is about 20:1 to about 5:1, about 18:1 to about 10:1, or about 16:1 to about 12:1.

In certain embodiments, the stabilizer (or mixture of stabilizers) is part of an aqueous medium of the invention and is present at a concentration of about 0.05 mg/ml to about 100.0 mg/ml, about 0.1 mg/ml to about 80.0 mg/ml, about 0.2 mg/ml to about 60.0 mg/ml, about 0.3 mg/ml to about 40.0 mg/ml, about 0.4 mg/ml to about 20.0 mg/ml, about 0.5 mg/ml to about 15.0 mg/ml, about 1.0 mg/ml to about 10.0 mg/ml, or about 1.5 mg/ml to about 5.0 mg/ml.

In certain embodiments, the stabilizer (or mixture of stabilizers) is part of an aqueous medium of the invention and is present at a concentration of about 0.05 mg/ml to about 10.0 mg/ml, about 0.1 mg/ml to about 8.0 mg/ml, about 0.2 mg/ml to about 6.0 mg/ml, about 0.3 mg/ml to about 5.0 mg/ml, about 0.4 mg/ml to about 4.0 mg/ml, about 0.5 mg/ml to about 3.0 mg/ml, about 0.6 mg/ml to about 2.5 mg/ml, or about 0.7 mg/ml to about 2.0 mg/ml.

In certain embodiments, the stabilizer is part of an aqueous medium of the invention and is present at a concentration of about 5 mM to about 500 mM, about 6 mM to about 400 mM, about 7 mM to about 300 mM, about 8 mM to about 250 mM, about 9 mM to about 200 mM, about 10 mM to about 150 mM, about 15 mM to about 100 mM, or about 20 mM to about 50 mM. In certain embodiments, the stabilizer is part of an aqueous medium of the invention and is present at a concentration of about 0.1 mM to about 100 mM, about 0.2 mM to about 80 mM, about 0.3 mM to about 60 mM, about 0.4 mM to about 40 mM, about 0.5 mM to about 30 mM, about 0.6 mM to about 25 mM, about 0.7 mM to about 20 mM, about 0.8 to about 15 mM, about 0.9 mM to about 12.5 mM, or about 1.0 mM to about 10 mM.

In certain embodiments, compositions of the invention further comprise a plasticizer. For example, in certain embodiments, the compositions comprise an inorganic compound and a plasticizer. As used herein, a "plasticizer" is any agent capable of facilitating or improving the storage function of a dry-state matrix. Thus, in certain embodiments, the plasticizer improves the mechanical properties (e.g., flexibility) of a dry-state matrix. In certain embodiments, the plasticizer improves the durability (e.g., resistance to vibrational damage) of a dry-state matrix. In certain embodiments, the plasticizer facilitates the reversible dissociation between inorganic compounds and biomolecules upon re-hydration of a dry-state matrix. In other embodiments, the plasticizer facilitates the reversible dissociation between stabilizers and biomolecules upon re-hydration of a dry-state matrix.

In certain embodiments, the plasticizer does not substantially interfere with the properties of biomolecules stored in a dry-state matrix of the invention (e.g., does not interfere with the chemical or physical stability of stored biomolecules). In other embodiments, the plasticizer inhibits microbial growth (e.g., bacterial or fungal growth) during storage of the dry-state matrices of the invention.

In certain embodiments, the plasticizer is a poly-alcohol. As used herein, a "poly-alcohol" is an organic compound having two or more hydroxyl groups. In certain embodiments, the plasticizer is a long-chain poly-alcohol (e.g., polyvinyl alcohol or polyserine). In certain embodiments, the plasticizer is a sugar (e.g., a monosaccharide, a disaccharide, or a complex sugar). Monosaccharides include, but are not limited to, hexoses, pentoses, tetroses, sedoheptulose, glucose, mannose, galactose, allose, altrose, gulose, idose, talose, fructose, sorbose, psicose, tagatose, fucose, fuculose, rhamnose, ribose, arabinose, xylose, lyxose, ribulose, xylulose, deoxyribose, erythrulose, erythrose, threose, dihydroxyacetone, and glyceraldehyde. Disaccharides include, but are not limited to, sucrose, lactose, trehalose, and maltose. Complex sugars include, but are not limited to, trisaccharides, tetrasaccharides, polysaccharides, glycosaminoglycans, aminoglycosidase, raffinose, melezitose, maltotriose, acarbose, stachyose, fructo-oligosaccharide, galacto-oligosaccharide, mannan-oligosaccharide, glycogen, starch, amylose, amylopectin, cellulose, chitin, inulin, dextrin, glucan (e.g., beta-glucan, dextran), heparin, chondroitin sulfate, hyaluronan, heparin sulfate, dermatan sulfate, keratan sulfate, kanamycin, streptomycin, tobramycin, neomycin, paromomycin, apramycin, gentamycin, netilmycin, and amikacin.

In certain embodiments, the plasticizer is a short-chain poly-alcohol (e.g., a linear or branched short chain poly-alcohol). As used herein, a "short-chain" poly-alcohol is a poly-alcohol having a backbone of six or fewer carbon atoms. In certain embodiments, the short-chain poly-alcohol includes twelve or fewer carbon atoms. In certain embodiments, the short-chain poly-alcohol is linear and has the general formula $C_n(OH)_m H_{2n+2-m}$ where n=2 to 6 and m=2 ton. In certain embodiments, the short-chain poly-alcohol is linear and has the general formula $C_n(OH)_m H_{2n+2-m}$ where n=2 to 12 and m=2 to n. In certain embodiments, the short-chain poly-alcohol is branched and has the general formula $C_n(OH)_m H_{2n+2-m}$ where n=4 to 6 and m=2 ton. In certain embodiments, the short-chain poly-alcohol is branched and has the general formula $C_n(OH)_m H_{2n+2-m}$ where n=4 to 12 and m=2 ton. Short-chain poly-alcohols of the invention include, but are not limited to, ethylene glycol, 1-3 propane diol, glycerol, butane triol (e.g., n-butane triol or isobutane triol), erythritol, pentane triol (e.g., n-pentane triol or isopentane triol), pentane tetraol (e.g., n-pentane tetraol, isopentane tetraol), pentaerythritol, xylitol, sorbitol and mannitol.

In certain embodiments, the plasticizer is a short-chain polyol selected from the group consisting of ethylene glycol, 1,3-propane diol, glycerol, and erythritol. In other embodiments, the plasticizer is glucose. In other embodiments, the plasticizer is sucrose, trehalose, or mannose. In other embodiments, the plasticizer is ficol or dextran (e.g., short-chain dextran having a MW less than 10 kD). In still other embodiments, the plasticizer is polyvinyl alcohol or polyserine. Thus, for example, addition of ethylene glycol, 1,3-propane diol, glycerol, erythritol, glucose, sucrose, trehalose, mannose, ficol, dextran, polyvinyl alcohol, or polyserine to a dry-state composition of the invention renders the composition (e.g., matrix) more resistant to vibrational damage and facilitates reversible dissociation of the air-dried matrix upon re-hydration.

In certain embodiments, the plasticizer is a poly-alcohol, wherein the poly-alcohol is not a monosaccharide. In certain embodiments, the plasticizer is a poly-alcohol, wherein the poly-alcohol is not a hexose. In certain embodiments, the plasticizer is a poly-alcohol, wherein the poly-alcohol is not a pentose. In certain embodiments, the plasticizer is a poly-alcohol, wherein the poly-alcohol is not a tetrose. In certain embodiments, the plasticizer is a poly-alcohol, wherein the poly-alcohol is not one or more monosaccharides selected from the group consisting of sedoheptulose, glucose, mannose, galactose, allose, altrose, gulose, idose, talose, fructose, sorbose, psicose, tagatose, fucose, fuculose, rhamnose, ribose, arabinose, xylose, lyxose, ribulose, xylulose, deoxyribose, erythrulose, erythrose, threose, dihydroxyacetone, and glyceraldehyde.

In certain embodiments, the plasticizer is a poly-alcohol, wherein the poly-alcohol is not a disaccharide. In certain embodiments, the plasticizer is not one or more disaccharides selected from the group consisting of sucrose, lactose, trehalose, and maltose.

In certain embodiments, the plasticizer is a poly-alcohol, wherein the poly-alcohol is not a complex sugar. In certain embodiments, the plasticizer is a poly-alcohol, wherein the poly-alcohol is not a trisaccharide. In certain embodiments, the plasticizer is a poly-alcohol, wherein the poly-alcohol is not a tetrasaccharide. In certain embodiments, the plasticizer is a poly-alcohol, wherein the poly-alcohol is not a polysaccharide. In certain embodiments, the plasticizer is a poly-alcohol, wherein the poly-alcohol is not a glycosaminoglycan. In certain embodiments, the plasticizer is a poly-alcohol, wherein the poly-alcohol is not an aminoglycosidase. In certain embodiments, the plasticizer is a poly-alcohol, wherein the poly-alcohol is not one or more complex sugars selected from the group consisting of raffinose, melezitose, maltotriose, acarbose, stachyose, fructo-oligosaccharide, galacto-oligosaccharide, mannan-oligosaccharide, glycogen, starch, amylose, amylopectin, cellulose, chitin, inulin, dextrin, glucan (e.g., beta-glucan, dextran), heparin, chondroitin sulfate, hyaluronan, heparin sulfate, dermatan sulfate, keratan sulfate, kanamycin, streptomycin, tobramycin, neomycin, paromomycin, apramycin, gentamycin, netilmycin, and amikacin.

In certain embodiments, the compositions of the invention comprise an inorganic compound, a stabilizer, and a plasticizer. In certain embodiments, the compositions comprise an inorganic compound, two or more stabilizers, and a plasticizer. The inorganic compound and the stabilizers can be any inorganic compound and stabilizer described herein.

In certain embodiments, the ratio of inorganic compounds to plasticizers in the composition is about 20:1 to about 1:2, about 15:1 to about 1:1.5, 12:1 to about 1:1, about 10:1 to about 1.5:1, about 8:1 to about 2:1 by weight. In other embodiments, the ratio of inorganic compounds to plasticizers is about 500:1 to about 50:1, about 480:1 to about 100:1, about 460:1 to about 150:1, about 440:1 to about 200:1, about 420:1 to about 250:1, or about 400:1 to about 300:1.

In certain embodiments, the plasticizer is part of an aqueous medium of the invention and is present at a concentration of about 0.01% to about 10%, about 0.02% to about 8%, about 0.03% to about 5%, about 0.04% to about 2%, about 0.05% to about 1%, or about 0.06% to about 0.5%.

In certain embodiments, the compositions of the invention further comprise one or more RNase inhibitors. For example, in certain embodiments, the compositions comprise an inorganic compound and an RNase inhibitor. RNase inhibitors include, but are not limited to, 2'-cytidine monophosphate free acid (2'-CMP), aluminon, adenosine 5'-pyrophosphate, 5'-diphosphoadenosine 3'-phosphate (ppA-3'-p), 5'-diphosphoadenosine 2'-phosphate (ppA-2'-p), Leucine, poly-L-aspartic acid, tyrosine-glutamic acid polymer, oligovinysulfonic acid, 5'-phopho-2'-deoxyuridine 3'-pyrophosphate P' 5'-ester with adenosine 3'-phosphate (pdUppAp). In certain embodiments, the compositions comprise two or more RNase inhibitors.

In certain embodiments, the compositions comprise 2'-CMP. In certain embodiments, the compositions further comprise 2'-CMP and aluminon. In certain embodiments, the compositions further comprise 2'-CMP and ppA-3'-p. In certain embodiments, the compositions further comprise 2'-CMP and Leucine. In certain embodiments, the compositions further comprise 2'-CMP and poly-L-aspartic acid. In certain embodiments, the compositions further comprise 2'-CMP and tyrosine glutamic acid polymer. In certain embodiments, the compositions further comprise 2'-CMP and oligovinysulfonic acid. In certain embodiments, the compositions further comprise 2'-CMP and pdUppAp. In certain embodiments, the compositions further comprise aluminon. In certain embodiments, the compositions further comprise aluminon and ppA-3'-p. In certain embodiments, the compositions further comprise aluminon and Leucine. In certain embodiments, the compositions further comprise aluminon and poly-L-aspartic acid. In certain embodiments, the compositions further comprise aluminon and tyrosine glutamic acid polymer. In certain embodiments, the compositions further comprise aluminon and oligovinysulfonic acid. In certain embodiments, the compositions further comprise aluminon and pdUppAp. In certain embodiments, the compositions further comprise ppA-3'-p. In certain embodiments, the compositions further comprise ppA-3'-p and Leucine. In certain embodiments, the compositions further comprise ppA-3'-p and poly-L-aspartic acid. In certain embodiments, the compositions further comprise ppA-3'-p and tyrosine glutamic acid polymer. In certain embodiments, the compositions further comprise ppA-3'-p and oligovinysulfonic acid. In certain embodiments, the compositions further comprise ppA-3'-p and pdUppAp. In certain embodiments, the compositions further comprise Leucine. In certain embodiments, the compositions further comprise Leucine and poly-L-aspartic acid. In certain embodiments, the compositions further comprise Leucine and tyrosine glutamic acid polymer. In certain embodiments, the compositions further comprise Leucine and oligovinysulfonic acid. In certain embodiments, the compositions further comprise Leucine and pdUppAp. In certain embodiments, the compositions further comprise poly-L-aspartic acid. In certain embodiments, the compositions further comprise poly-L-aspartic acid and tyrosine glutamic acid polymer. In certain embodiments, the compositions further comprise poly-L-aspartic acid and oligovinysulfonic acid. In certain embodiments, the compositions further comprise poly-L-aspartic acid and pdUppAp. In certain embodiments, the compositions further comprise tyrosine glutamic acid polymer. In certain embodiments, the compositions further comprise tyrosine glutamic acid polymer and oligovinysulfonic acid. In certain embodiments, the compositions further comprise tyrosine glutamic acid polymer and pdUppAp. In certain embodiments, the compositions further comprise oligovinysulfonic acid. In certain embodiments, the compositions further comprise oligovinysulfonic acid and pdUppAp.

In certain embodiments, the RNase inhibitor is part of an aqueous medium of the invention and is present at a concentration of about 1 mM to about 250 mM, about 1 mM to about 200 mM, about 1 mM to about 150 mM, about 1 mM to about 100 mM, about 2 mM to about 50 mM, about 3 mM to about 40 mM, about 4 mM to about 30 mM, about 5 mM to about 20 mM, about 6 mM to about 15 mM, or about 10 mM. In certain embodiments, the RNase inhibitor is part of an aqueous medium of the invention and is present at a concentration of about 1 µM to about 500 µM, about 1 µM to about 400 µM, about 1 µM to about 300 µM, about 1 µM to about 200 µM, about 1 µM to about 100 µM, about 1 µM to about 50 µM, about 2 µM to about 40 µM, about 3 µM to about 30 µM, about 4 µM to about 20 µM, about 5 µM to about 15 µM, or about 10 µM.

In certain embodiments, the compositions comprise an inorganic compound, a stabilizing agent, and an RNase inhibitor. In certain embodiments, the compositions comprise an inorganic compound, a stabilizing agent, a plasticizer, and an RNase inhibitor. In certain embodiments, the compositions comprise an inorganic compound, a metal chelator, and an RNase inhibitor. In certain embodiments, the compositions comprise an inorganic compound, a metal chelator, a plasticizer, and an RNase inhibitor. In certain embodiments, the compositions comprise an inorganic compound, at least two stabilizing agents, including at least one metal chelator, and an RNase inhibitor. In certain embodiments, the compositions comprise an inorganic compound, at least two stabilizing agents, including a metal chelator, a plasticizer, and an RNase inhibitor.

In certain embodiments, the compositions of the invention further comprise biomolecules. Thus, for example, any of the compositions described herein can further include biomolecules. In certain embodiments, the compositions comprise a biological sample that contains biomolecules, such as a bodily fluid (e.g., blood, serum, cerebrospinal fluid, urine, sputum, semen, etc.), a tissue sample (e.g., a piece of solid tissue, such as a tissue biopsy, a tissue homogenate, a hair sample, etc.), a cellular lysate (e.g., a blood cell lysate, a skin cell lysate, etc.), or a fraction thereof. In other embodiments, the compositions comprise a purified or synthetic sample of biomolecules (e.g., a purified or synthetic nucleic acid or protein sample). In certain embodiments, the storage compositions comprise small molecules isolated from biological samples (i.e., small molecules that are neither synthetic nor industrially produced). In certain embodiments, the storage compositions comprise one or more types of small molecules selected from the group consisting of lipids, coenzymes, metabolites, pharmaceutical agents, and metabolites of pharmaceutical agents, wherein said small molecules were isolated from biological samples.

In certain embodiments, the compositions comprise genomic DNA. In certain embodiments, the compositions comprise DNA having a length greater than about 0.1 kB, 0.2 kB, 0.3 kB, 0.5 kB, 0.75 kB, 1 kB, 5 kB, 10 kB, 15 kB, 20 kB, 25 kB, 30 kB, 35 kB, 40 kB, 45 kB, 50 kB, or longer. In certain embodiments, the compositions safely store genomic DNA such that genomic DNA fragments having a length greater than about 0.1 kB, 0.2 kB, 0.3 kB, 0.5 kB, 0.75 kB, 1 kB, 2 kB, 3 kB, 5 kB, 10 kB, 15 kB, 20 kB, 25 kB, 30 kB, 35 kB, 40 kB, 45 kB, 50 kB, or longer can be recovered.

In certain embodiments, the compositions comprise RNA. In certain embodiments, the RNA is present in a crude lysate, a partially purified sample, or a purified RNA fraction from a sample. In certain embodiments, the RNA is mRNA. In other embodiments, the RNA is rRNA or tRNA. In other embodiments, the RNA is siRNA. In still other embodiments, the RNA is total RNA.

In certain embodiments, the ratio of inorganic compound to biomolecules in the composition is about 20000:1 to about 2:1 by weight. In other embodiments, the ratio of inorganic compound to biomolecules in the composition is about 10000:1 to about 1000:1 by weight. In other embodiments, the ratio of inorganic compound to biomolecules is about 1000:1 to about 100:1 by weight. In other embodiments, the ratio of inorganic compound to biomolecules is about 100:1 to about 10:1 by weight. In other embodiments, the ratio of inorganic compound to biomolecules is about 10:1 to about 1:1. In other embodiments, the ratio of inorganic compound to biomolecules is about 5:1 to about 1:5. In other embodiments, the ratio of inorganic compound to biomolecules in the composition is about 5000:1 to about 50:1, about 1000:1 to about 10:1, about 500:1 to about 5:1, about 100:1 to about 2:1, or about 50:1 to about 1:2 by weight. In still other embodiments, the ration of inorganic compound to biomolecules is about 50:1, about 40:1, about 30:1, about 20:1, about 10:1, or about 1:1 by weight.

In certain embodiments, the compositions comprise a water soluble inorganic compound (e.g., a compound comprising boron, phosphorus, vanadium, or aluminum), a singlet oxygen quencher (e.g., an alkyl imidazole, an indole, and/or a sulfur-containing amino acid) and, optionally, biomolecules. In other embodiments, the compositions comprise a water soluble inorganic compound (e.g., a compound comprising boron, phosphorus, vanadium, or aluminum), a singlet oxygen quencher (e.g., an alkyl imidazole, an indole, and/or a sulfur-containing amino acid), a plasticizer (e.g., glycerol, polyvinyl alcohol, trehalose, and/or dextran) and, optionally, biomolecules. In other embodiments, the compositions comprise a water soluble inorganic compound (e.g., a compound comprising boron, phosphorus, vanadium, or aluminum), a singlet oxygen quencher (e.g., an alkyl imidazole, an indole, and/or a sulfur-containing amino acid), a plasticizer (e.g., glycerol, polyvinyl alcohol, trehalose, and/or dextran), a metal chelator (e.g., EDTA) and, optionally, biomolecules.

In certain embodiments, the compositions comprise a water soluble inorganic compound (e.g., a compound comprising boron, phosphorus, vanadium, or aluminum), a hydroxyl radical scavenger and, optionally, biomolecules. In other embodiments, the compositions comprise a water soluble inorganic compound (e.g., a compound comprising boron, phosphorus, vanadium, or aluminum), a hydroxyl radical scavenger, a plasticizer (e.g., glycerol, polyvinyl alcohol, trehalose, and/or dextran) and, optionally, biomolecules. In other embodiments, the compositions comprise a water soluble inorganic compound (e.g., a compound comprising boron, phosphorus, vanadium, or aluminum), a hydroxyl radical scavenger, a plasticizer (e.g., glycerol, polyvinyl alcohol, trehalose, and/or dextran), a metal chelator (e.g., EDTA) and, optionally, biomolecules.

In certain embodiments, the compositions comprise a water soluble inorganic compound (e.g., a compound comprising boron, phosphorus, vanadium, or aluminum), a hydroperoxide removing agent and, optionally, biomolecules. In other embodiments, the compositions comprise a water soluble inorganic compound (e.g., a compound comprising boron, phosphorus, vanadium, or aluminum), a hydroperoxide removing agent, a plasticizer (e.g., glycerol, polyvinyl alcohol, trehalose, and/or dextran) and, optionally, biomolecules. In other embodiments, the compositions comprise a water soluble inorganic compound (e.g., a compound comprising boron, phosphorus, vanadium, or aluminum), a hydroperoxide removing agent, a plasticizer (e.g., glycerol, polyvinyl alcohol, trehalose, and/or dextran), a metal chelator (e.g., EDTA) and, optionally, biomolecules.

In certain embodiments, the compositions comprise a water soluble inorganic compound (e.g., a compound comprising boron, phosphorus, vanadium, or aluminum), a hydroxyl radical scavenger, a hydroperoxide removing agent and, optionally, biomolecules. In other embodiments, the compositions comprise a water soluble inorganic compound (e.g., a compound comprising boron, phosphorus, vanadium, or aluminum), a hydroxyl radical scavenger, a hydroperoxide removing agent, a plasticizer (e.g., glycerol, polyvinyl alcohol, trehalose, and/or dextran) and, optionally, biomolecules. In other embodiments, the compositions comprise a water soluble inorganic compound (e.g., a compound comprising boron, phosphorus, vanadium, or aluminum), a hydroxyl radical scavenger, a hydroperoxide removing agent, a plasticizer (e.g., glycerol, polyvinyl alcohol, trehalose, and/or dextran), a metal chelator (e.g., EDTA) and, optionally, biomolecules.

In certain embodiments, the compositions comprise boric acid, histidine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, histidine, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, histidine, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, tryptophan, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, tyrosine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, ascorbate and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, azide (e.g., sodium azide) and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, tocopherol and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, carotene and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, o-phenanthroline and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, sodium lauryl sarcosyl and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise boric acid, guanidium hydrochloride and, optionally, a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions comprise borate, histidine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, histidine, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, histidine, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, tryptophan, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, tyrosine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, ascorbate and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, azide (e.g., sodium azide) and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, tocopherol and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, carotene and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, o-phenanthroline and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, sodium lauryl sarcosyl and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise borate, guanidium hydrochloride and, optionally, a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions comprise phosphoric acid, histidine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, histidine, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, histidine, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, tryptophan, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, tyrosine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, ascorbate and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, azide (e.g., sodium azide) and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, tocopherol and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, carotene and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, o-phenanthroline and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, sodium lauryl sarcosyl and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise phosphoric acid, guanidium hydrochloride and, optionally, a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions comprise a salt of phosphoric acid, histidine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, histidine, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, histidine, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, tryptophan, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, tyrosine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, ascorbate and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, azide (e.g., sodium azide) and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, tocopherol and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, carotene and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, o-phenanthroline and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, sodium lauryl sarcosyl and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a salt of phosphoric acid, guanidium hydrochloride and, optionally, a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions comprise a vanadate salt, histidine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, histidine, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, histidine, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, tryptophan, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, tyrosine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, ascorbate and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, azide (e.g., sodium azide) and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, tocopherol and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, carotene and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, o-phenanthroline and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, sodium lauryl sarcosyl and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise a vanadate salt, guanidium hydrochloride and, optionally, a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions comprise potassium alum, histidine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, histidine, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, histidine, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, tryptophan, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, tyrosine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, ascorbate and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, azide (e.g., sodium azide) and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, tocopherol and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, carotene and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, o-phenanthroline and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, sodium lauryl sarcosyl and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise potassium alum, guanidium hydrochloride and, optionally, a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions comprise soda alum, histidine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, histidine, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, histidine, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, tryptophan, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, tyrosine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, ascorbate and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, azide (e.g., sodium azide) and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, tocopherol and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, carotene and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, o-phenanthroline and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, sodium lauryl sarcosyl and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise soda alum, guanidium hydrochloride and, optionally, a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions comprise ammonium alum, histidine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, histidine, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, histidine, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, tryptophan and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, tryptophan, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, methionine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, tyrosine and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, ascorbate and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, azide (e.g., sodium azide) and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, tocopherol and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, carotene and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, o-phenanthroline and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, sodium lauryl sarcosyl and, optionally, a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ammonium alum, guanidium hydrochloride and, optionally, a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the inorganic compounds of the foregoing compositions (e.g., boric acid, borate, phosphoric acid, salts of phosphoric acid, vanadate salts, potassium alum, soda alum, and ammonium alum) are in an aqueous medium (e.g., either before or after being mixed with a sample) and have a concentration of about 5 mM to about 500 mM, about 6 mM to about 400 mM, about 7 mM to about 300 mM, about 8 mM to about 250 mM, about 9 mM to about 200 mM, about 10 mM to about 150 mM, about 20 mM to about 140 mM, about 30 mM to about 130 mM, about 40 mM to about 120 mM, about 50 mM to about 110 mM, about 60 mM to about 100 mM, about 70 mM to about 90 mM, or about 80 mM. In certain embodiments, the stabilizers of the foregoing compositions (e.g., histidine, tryptophan, methionine, tyrosine, ascorbate, sodium azide, tocopherol, carotene, o-phenanthroline, sodium lauryl sarcosyl, and guanidium HCl) are in an aqueous medium (e.g., either before or after being mixed with a sample) and have a concentration of about 1 mM to about 250 mM, about 2 mM to about 200 mM, about 3 mM to about 150 mM, about 4 mM to about 100 mM, about 5 mM to about 75 mM, about 10 mM to about 50 mM, about 15 mM to about 45 mM, about 20 mM to about 40 mM, about 25 mM to about 35 mM, or about 30 mM. In certain embodiments, the plasticizers of the foregoing compositions (e.g., ethylene glycol, 1,3-propane diol, glycerol, erythritol, glucose, sucrose, trehalose, mannose, dextran, polyvinyl alcohol and polyserine) are in an aqueous medium (e.g., either before or after being mixed with a sample) and have a concentration of about 0.01% to about 8.0%, about 0.02% to about 5.0%, about 0.03% to about 2.0%, about 0.04% to about 1.5%, about 0.05% to about 1%, or about 0.06% to about 0.5%.

In certain embodiments, the compositions comprise boric acid and dimethyl sulfoxide. In certain embodiments, the compositions comprise boric acid, dimethyl sulfoxide, and catalase. In certain embodiments, the compositions comprise boric acid, dimethyl sulfoxide, and pyruvate. In certain embodiments, the compositions comprise boric acid, dimethyl sulfoxide, and glutathione. In certain embodiments, the compositions comprise boric acid, dimethyl sulfoxide, and a glutathione peroxidase. In certain embodiments, the compositions comprise boric acid and histidine. In certain embodiments, the compositions comprise boric acid, histidine, and catalase. In certain embodiments, the compositions comprise boric acid, histidine, and pyruvate. In certain embodiments, the compositions comprise boric acid, histidine, and glutathione. In certain embodiments, the compositions comprise boric acid, histidine, and a glutathione peroxidase. In certain embodiments, the compositions comprise boric acid and mannitol. In certain embodiments, the compositions comprise boric acid, mannitol, and catalase. In certain embodiments, the compositions comprise boric acid, mannitol, and pyruvate. In certain embodiments, the compositions comprise boric acid, mannitol, and glutathione. In certain embodiments, the compositions comprise boric acid, mannitol, and a glutathione peroxidase. In certain embodiments, the compositions comprise boric acid and sucrose. In certain embodiments, the compositions comprise boric acid, sucrose, and catalase. In certain embodiments, the compositions comprise boric acid, sucrose, and pyruvate. In certain embodiments, the compositions comprise boric acid, sucrose, and glutathione. In certain embodiments, the compositions comprise boric acid, sucrose, and a glutathione peroxidase. In certain embodiments, the compositions comprise boric acid and glucose. In certain embodiments, the compositions comprise boric acid, glucose, and catalase. In certain embodiments, the compositions comprise boric acid, glucose, and pyruvate. In certain embodiments, the compositions comprise boric acid, glucose, and glutathione. In certain embodiments, the compositions comprise boric acid, glucose, and a glutathione peroxidase. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions of the immediately foregoing paragraph further comprise EDTA. In certain embodiments, the compositions of the immediately foregoing paragraph further comprise EDTA and glycerol. In certain embodiments, the compositions of the immediately foregoing paragraph further comprise EDTA and trehalose. In certain embodiments, the compositions of the immediately foregoing paragraph further comprise EDTA and dextran. In certain embodiments, the compositions of the immediately foregoing paragraph further comprise EDTA and polyvinyl alcohol. In certain embodiments, the compositions of the immediately foregoing paragraph further comprise EGTA. In certain embodiments, the compositions of the immediately foregoing paragraph further comprise EGTA and glycerol. In certain embodiments, the compositions of the immediately foregoing paragraph further comprise EGTA and trehalose. In certain embodiments, the compositions of the immediately foregoing paragraph further comprise EGTA and dextran. In certain embodiments, the compositions of the immediately foregoing paragraph further comprise EGTA and polyvinyl alcohol. In certain embodiments, the compositions of the immediately foregoing paragraph further comprise o-phenanthroline. In certain embodiments, the compositions of the immediately foregoing paragraph further comprise o-phenanthroline and glycerol. In certain embodiments, the compositions of the immediately foregoing paragraph further comprise o-phenanthroline and trehalose. In certain embodiments, the compositions of the immediately foregoing paragraph further comprise o-phenanthroline and dextran. In certain embodiments, the compositions of the immediately foregoing paragraph further comprise o-phenanthroline and polyvinyl alcohol. In certain embodiments, the compositions of the immediately foregoing paragraph further comprise EDTA and citrate. In certain embodiments, the compositions of the immediately foregoing paragraph further comprise EDTA, citrate, and glycerol. In certain embodiments, the compositions of the immediately foregoing paragraph further comprise EDTA, citrate, and trehalose. In certain embodiments, the compositions of the immediately foregoing paragraph further comprise EDTA, citrate, and dextran. In certain embodiments, the compositions of the immediately foregoing paragraph further comprise EDTA, citrate, and polyvinyl alcohol. In certain embodiments, the compositions of the immediately foregoing paragraph further comprise EGTA and citrate. In certain embodiments, the compositions of the immediately foregoing paragraph further comprise EGTA, citrate, and glycerol. In certain embodiments, the compositions of the immediately foregoing paragraph further comprise EGTA, citrate, and trehalose. In certain embodiments, the compositions of the immediately foregoing paragraph further comprise EGTA, citrate, and dextran. In certain embodiments, the compositions of the immediately foregoing paragraph further comprise EGTA, citrate, and polyvinyl alcohol. In certain embodiments, the compositions of the immediately foregoing paragraph further comprise o-phenanthroline and citrate. In certain embodiments, the compositions of the immediately foregoing paragraph further comprise o-phenanthroline, citrate, and glycerol. In certain embodiments, the compositions of the immediately foregoing paragraph further comprise o-phenanthroline, citrate, and trehalose. In certain embodiments, the compositions of the immediately foregoing paragraph further comprise o-phenanthroline, citrate, and dextran. In certain embodiments, the compositions of the immediately foregoing paragraph further comprise o-phenanthroline, citrate, and polyvinyl alcohol.

In certain embodiments, the compositions comprise borate and dimethyl sulfoxide. In certain embodiments, the compositions comprise borate, dimethyl sulfoxide, and catalase. In certain embodiments, the compositions comprise borate, dimethyl sulfoxide, and pyruvate. In certain embodiments, the compositions comprise borate, dimethyl sulfoxide, and glutathione. In certain embodiments, the compositions comprise borate, dimethyl sulfoxide, and a glutathione peroxidase. In certain embodiments, the compositions comprise borate and histidine. In certain embodiments, the compositions comprise borate, histidine, and catalase. In certain embodiments, the compositions comprise borate, histidine, and pyruvate. In certain embodiments, the compositions comprise borate, histidine, and glutathione. In certain embodiments, the compositions comprise borate, histidine, and a glutathione peroxidase. In certain embodiments, the compositions comprise borate and mannitol. In certain embodiments, the compositions comprise borate, mannitol, and catalase. In certain embodiments, the compositions comprise borate, mannitol, and pyruvate. In certain embodiments, the compositions comprise borate, mannitol, and glutathione. In certain embodiments, the compositions comprise borate, mannitol, and a glutathione peroxidase. In certain embodiments, the compositions comprise borate and sucrose. In certain embodiments, the compositions comprise borate, sucrose, and catalase. In certain embodiments, the compositions comprise borate, sucrose, and pyruvate. In certain embodiments, the compositions comprise borate, sucrose, and glutathione. In certain embodiments, the compositions comprise borate, sucrose, and a glutathione peroxidase. In certain embodiments, the compositions comprise borate and glucose. In certain embodiments, the compositions comprise borate, glucose, and catalase. In certain embodiments, the compositions comprise borate, glucose, and pyruvate. In certain embodiments, the compositions comprise borate, glucose, and glutathione. In certain embodiments, the compositions comprise borate, glucose, and a glutathione peroxidase. Each of the embodiments of this paragraph can further comprise an RNase inhibitor (e.g., any RNase inhibitor described or suggested herein) and/or biomolecules (e.g., any sample comprising biomolecules, such as a biological sample).

In certain embodiments, the compositions of the immediately foregoing paragraph further comprise EDTA. In certain embodiments, the compositions of the immediately foregoing paragraph further comprise EDTA and glycerol. In certain embodiments, the compositions of the immediately foregoing paragraph further comprise EDTA and trehalose. In certain embodiments, the compositions of the immediately foregoing paragraph further comprise EDTA and dextran. In certain embodiments, the compositions of the immediately foregoing paragraph further comprise EDTA and polyvinyl alcohol. In certain embodiments, the compositions of the immediately foregoing paragraph further comprise EGTA. In certain embodiments, the compositions of the immediately foregoing paragraph further comprise EGTA and glycerol. In certain embodiments, the compositions of the immediately foregoing paragraph further comprise EGTA and trehalose. In certain embodiments, the compositions of the immediately foregoing paragraph further comprise EGTA and dextran. In certain embodiments, the compositions of the immediately foregoing paragraph further comprise EGTA and polyvinyl alcohol. In certain embodiments, the compositions of the immediately foregoing paragraph further comprise o-phenanthroline. In certain embodiments, the compositions of the immediately foregoing paragraph further comprise o-phenanthroline and glycerol. In certain embodiments, the compositions of the immediately foregoing paragraph further comprise o-phenanthroline and trehalose. In certain embodiments, the compositions of the immediately foregoing paragraph further comprise o-phenanthroline and dextran. In certain embodiments, the compositions of the immediately foregoing paragraph further comprise o-phenanthroline and polyvinyl alcohol. In certain embodiments, the compositions of the immediately foregoing paragraph further comprise EDTA and citrate. In certain embodiments, the compositions of the immediately foregoing paragraph further comprise EDTA, citrate, and glycerol. In certain embodiments, the compositions of the immediately foregoing paragraph further comprise EDTA, citrate, and trehalose. In certain embodiments, the compositions of the immediately foregoing paragraph further comprise EDTA, citrate, and dextran. In certain embodiments, the compositions of the immediately foregoing paragraph further comprise EDTA, citrate, and polyvinyl alcohol. In certain embodiments, the compositions of the immediately foregoing paragraph further comprise EGTA and citrate. In certain embodiments, the compositions of the immediately foregoing paragraph further comprise EGTA, citrate, and glycerol. In certain embodiments, the compositions of the immediately foregoing paragraph further comprise EGTA, citrate, and trehalose. In certain embodiments, the compositions of the immediately foregoing paragraph further comprise EGTA, citrate, and dextran. In certain embodiments, the compositions of the immediately foregoing paragraph further comprise EGTA, citrate, and polyvinyl alcohol. In certain embodiments, the compositions of the immediately foregoing paragraph further comprise o-phenanthroline and citrate. In certain embodiments, the compositions of the immediately foregoing paragraph further comprise o-phenanthroline, citrate, and glycerol. In certain embodiments, the compositions of the immediately foregoing paragraph further comprise o-phenanthroline, citrate, and trehalose. In certain embodiments, the compositions of the immediately foregoing paragraph further comprise o-phenanthroline, citrate, and dextran. In certain embodiments, the compositions of the immediately foregoing paragraph further comprise o-phenanthroline, citrate, and polyvinyl alcohol.

In certain embodiments, the compositions comprise phosphoric acid or a salt thereof and dimethyl sulfoxide. In certain embodiments, the compositions comprise phosphoric acid or a salt thereof, dimethyl sulfoxide, and catalase. In certain embodiments, the compositions comprise phosphoric acid or a salt thereof, dimethyl sulfoxide, and pyruvate. In certain embodiments, the compositions comprise phosphoric acid or a salt thereof, dimethyl sulfoxide, and glutathione. In certain embodiments, the compositions comprise phosphoric acid or a salt thereof, dimethyl sulfoxide, and a glutathione peroxidase. In certain embodiments, the compositions comprise phosphoric acid or a salt thereof and histidine. In certain embodiments, the compositions comprise phosphoric acid or a salt thereof, histidine, and catalase. In certain embodiments, the compositions comprise phosphoric acid or a salt thereof, histidine, and pyruvate. In certain embodiments, the compositions comprise phosphoric acid or a salt thereof, histidine, and glutathione. In certain embodiments, the compositions comprise phosphoric acid or a salt thereof, histidine, and a glutathione peroxidase. In certain embodiments, the compositions comprise phosphoric acid or a salt thereof and mannitol. In certain embodiments, the compositions comprise phosphoric acid or a salt thereof, mannitol, and catalase. In certain embodiments, the compositions comprise phosphoric acid or a salt thereof, mannitol, and pyruvate. In certain embodiments, the compositions comprise phosphoric acid or a salt thereof, mannitol, and glutathione. In certain embodiments, the compositions comprise phosphoric acid or a salt thereof, mannitol, and a glutathione peroxidase. In certain embodiments, the compositions comprise phosphoric acid or a salt thereof and sucrose. In certain embodiments, the compositions comprise phosphoric acid or a salt thereof, sucrose, and catalase. In certain embodiments, the compositions comprise phosphoric acid or a salt thereof, sucrose, and pyruvate. In certain embodiments, the compositions comprise phosphoric acid or a salt thereof, sucrose, and glutathione. In certain embodiments, the compositions comprise phosphoric acid or a salt thereof, sucrose, and a glutathione peroxidase. In certain embodiments, the compositions comprise phosphoric acid or a salt thereof and glucose. In certain embodiments, the compositions comprise phosphoric acid or a salt thereof, glucose, and catalase. In certain embodiments, the compositions comprise phosphoric acid or a salt thereof, glucose, and pyruvate. In certain embodiments, the compositions comprise phosphoric acid or a salt thereof, glucose, and glutathione. In certain embodiments, the compositions comprise phosphoric acid or a salt thereof, glucose, and a glutathione peroxidase. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions of the immediately foregoing paragraph further comprise EDTA. In certain embodiments, the compositions of the immediately foregoing paragraph further comprise EDTA and glycerol. In certain embodiments, the compositions of the immediately foregoing paragraph further comprise EDTA and trehalose. In certain embodiments, the compositions of the immediately foregoing paragraph further comprise EDTA and dextran. In certain embodiments, the compositions of the immediately foregoing paragraph further comprise EDTA and polyvinyl alcohol. In certain embodiments, the compositions of the immediately foregoing paragraph further comprise EGTA. In certain embodiments, the compositions of the immediately foregoing paragraph further comprise EGTA and glycerol. In certain embodiments, the compositions of the immediately foregoing paragraph further comprise EGTA and trehalose. In certain embodiments, the compositions of the immediately foregoing paragraph further comprise EGTA and dextran. In certain embodiments, the compositions of the immediately foregoing paragraph further comprise EGTA and polyvinyl alcohol. In certain embodiments, the compositions of the immediately foregoing paragraph further comprise o-phenanthroline. In certain embodiments, the compositions of the immediately foregoing paragraph further comprise o-phenanthroline and glycerol. In certain embodiments, the compositions of the immediately foregoing paragraph further comprise o-phenanthroline and trehalose. In certain embodiments, the compositions of the immediately foregoing paragraph further comprise o-phenanthroline and dextran. In certain embodiments, the compositions of the immediately foregoing paragraph further comprise o-phenanthroline and polyvinyl alcohol. In certain embodiments, the compositions of the immediately foregoing paragraph further comprise EDTA and citrate. In certain embodiments, the compositions of the immediately foregoing paragraph further comprise EDTA, citrate, and glycerol. In certain embodiments, the compositions of the immediately foregoing paragraph further comprise EDTA, citrate, and trehalose. In certain embodiments, the compositions of the immediately foregoing paragraph further comprise EDTA, citrate, and dextran. In certain embodiments, the compositions of the immediately foregoing paragraph further comprise EDTA, citrate, and polyvinyl alcohol. In certain embodiments, the compositions of the immediately foregoing paragraph further comprise EGTA and citrate. In certain embodiments, the compositions of the immediately foregoing paragraph further comprise EGTA, citrate, and glycerol. In certain embodiments, the compositions of the immediately foregoing paragraph further comprise EGTA, citrate, and trehalose. In certain embodiments, the compositions of the immediately foregoing paragraph further comprise EGTA, citrate, and dextran. In certain embodiments, the compositions of the immediately foregoing paragraph further comprise EGTA, citrate, and polyvinyl alcohol. In certain embodiments, the compositions of the immediately foregoing paragraph further comprise o-phenanthroline and citrate. In certain embodiments, the compositions of the immediately foregoing paragraph further comprise o-phenanthroline, citrate, and glycerol. In certain embodiments, the compositions of the immediately foregoing paragraph further comprise o-phenanthroline, citrate, and trehalose. In certain embodiments, the compositions of the immediately foregoing paragraph further comprise o-phenanthroline, citrate, and dextran. In certain embodiments, the compositions of the immediately foregoing paragraph further comprise o-phenanthroline, citrate, and polyvinyl alcohol.

In certain embodiments, the compositions comprise a vanadate salt and dimethyl sulfoxide. In certain embodiments, the compositions comprise a vanadate salt, dimethyl sulfoxide, and catalase. In certain embodiments, the compositions comprise a vanadate salt, dimethyl sulfoxide, and pyruvate. In certain embodiments, the compositions comprise a vanadate salt, dimethyl sulfoxide, and glutathione. In certain embodiments, the compositions comprise a vanadate salt, dimethyl sulfoxide, and a glutathione peroxidase. In certain embodiments, the compositions comprise a vanadate salt and histidine. In certain embodiments, the compositions comprise a vanadate salt, histidine, and catalase. In certain embodiments, the compositions comprise a vanadate salt, histidine, and pyruvate. In certain embodiments, the compositions comprise a vanadate salt, histidine, and glutathione. In certain embodiments, the compositions comprise a vanadate salt, histidine, and a glutathione peroxidase. In certain embodiments, the compositions comprise a vanadate salt and mannitol. In certain embodiments, the compositions comprise a vanadate salt, mannitol, and catalase. In certain embodiments, the compositions comprise a vanadate salt, mannitol, and pyruvate. In certain embodiments, the compositions comprise a vanadate salt, mannitol, and glutathione. In certain embodiments, the compositions comprise a vanadate salt, mannitol, and a glutathione peroxidase. In certain embodiments, the compositions comprise a vanadate salt and sucrose. In certain embodiments, the compositions comprise a vanadate salt, sucrose, and catalase. In certain embodiments, the compositions comprise a vanadate salt, sucrose, and pyruvate. In certain embodiments, the compositions comprise a vanadate salt, sucrose, and glutathione. In certain embodiments, the compositions comprise a vanadate salt, sucrose, and a glutathione peroxidase. In certain embodiments, the compositions comprise a vanadate salt and glucose. In certain embodiments, the compositions comprise a vanadate salt, glucose, and catalase. In certain embodiments, the compositions comprise a vanadate salt, glucose, and pyruvate. In certain embodiments, the compositions comprise a vanadate salt, glucose, and glutathione. In certain embodiments, the compositions comprise a vanadate salt, glucose, and a glutathione peroxidase. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions of the immediately foregoing paragraph further comprise EDTA. In certain embodiments, the compositions of the immediately foregoing paragraph further comprise EDTA and glycerol. In certain embodiments, the compositions of the immediately foregoing paragraph further comprise EDTA and trehalose. In certain embodiments, the compositions of the immediately foregoing paragraph further comprise EDTA and dextran. In certain embodiments, the compositions of the immediately foregoing paragraph further comprise EDTA and polyvinyl alcohol. In certain embodiments, the compositions of the immediately foregoing paragraph further comprise EGTA. In certain embodiments, the compositions of the immediately foregoing paragraph further comprise EGTA and glycerol. In certain embodiments, the compositions of the immediately foregoing paragraph further comprise EGTA and trehalose. In certain embodiments, the compositions of the immediately foregoing paragraph further comprise EGTA and dextran. In certain embodiments, the compositions of the immediately foregoing paragraph further comprise EGTA and polyvinyl alcohol. In certain embodiments, the compositions of the immediately foregoing paragraph further comprise o-phenanthroline. In certain embodiments, the compositions of the immediately foregoing paragraph further comprise o-phenanthroline and glycerol. In certain embodiments, the compositions of the immediately foregoing paragraph further comprise o-phenanthroline and trehalose. In certain embodiments, the compositions of the immediately foregoing paragraph further comprise o-phenanthroline and dextran. In certain embodiments, the compositions of the immediately foregoing paragraph further comprise o-phenanthroline and polyvinyl alcohol. In certain embodiments, the compositions of the immediately foregoing paragraph further comprise EDTA and citrate. In certain embodiments, the compositions of the immediately foregoing paragraph further comprise EDTA, citrate, and glycerol. In certain embodiments, the compositions of the immediately foregoing paragraph further comprise EDTA, citrate, and trehalose. In certain embodiments, the compositions of the immediately foregoing paragraph further comprise EDTA, citrate, and dextran. In certain embodiments, the compositions of the immediately foregoing paragraph further comprise EDTA, citrate, and polyvinyl alcohol. In certain embodiments, the compositions of the immediately foregoing paragraph further comprise EGTA and citrate. In certain embodiments, the compositions of the immediately foregoing paragraph further comprise EGTA, citrate, and glycerol. In certain embodiments, the compositions of the immediately foregoing paragraph further comprise EGTA, citrate, and trehalose. In certain embodiments, the compositions of the immediately foregoing paragraph further comprise EGTA, citrate, and dextran. In certain embodiments, the compositions of the immediately foregoing paragraph further comprise EGTA, citrate, and polyvinyl alcohol. In certain embodiments, the compositions of the immediately foregoing paragraph further comprise o-phenanthroline and citrate. In certain embodiments, the compositions of the immediately foregoing paragraph further comprise o-phenanthroline, citrate, and glycerol. In certain embodiments, the compositions of the immediately foregoing paragraph further comprise o-phenanthroline, citrate, and trehalose. In certain embodiments, the compositions of the immediately foregoing paragraph further comprise o-phenanthroline, citrate, and dextran. In certain embodiments, the compositions of the immediately foregoing paragraph further comprise o-phenanthroline, citrate, and polyvinyl alcohol.

In certain embodiments, the compositions comprise an alum (e.g., potassium alum, soda allum, or ammonium alum) and dimethyl sulfoxide. In certain embodiments, the compositions comprise an alum, dimethyl sulfoxide, and catalase. In certain embodiments, the compositions comprise an alum, dimethyl sulfoxide, and pyruvate. In certain embodiments, the compositions comprise an alum, dimethyl sulfoxide, and glutathione. In certain embodiments, the compositions comprise an alum, dimethyl sulfoxide, and a glutathione peroxidase. In certain embodiments, the compositions comprise an alum (e.g., potassium alum, soda allum, or ammonium alum) and histidine. In certain embodiments, the compositions comprise an alum, histidine, and catalase. In certain embodiments, the compositions comprise an alum, histidine, and pyruvate. In certain embodiments, the compositions comprise an alum, histidine, and glutathione. In certain embodiments, the compositions comprise an alum, histidine, and a glutathione peroxidase. In certain embodiments, the compositions comprise an alum (e.g., potassium alum, soda allum, or ammonium alum) and mannitol. In certain embodiments, the compositions comprise an alum, mannitol, and catalase. In certain embodiments, the compositions comprise an alum, mannitol, and pyruvate. In certain embodiments, the compositions comprise an alum, mannitol, and glutathione. In certain embodiments, the compositions comprise an alum, mannitol, and a glutathione peroxidase. In certain embodiments, the compositions comprise an alum (e.g., potassium alum, soda allum, or ammonium alum) and sucrose. In certain embodiments, the compositions comprise an alum, sucrose, and catalase. In certain embodiments, the compositions comprise an alum, sucrose, and pyruvate. In certain embodiments, the compositions comprise an alum, sucrose, and glutathione. In certain embodiments, the compositions comprise an alum, sucrose, and a glutathione peroxidase. In certain embodiments, the compositions comprise an alum (e.g., potassium alum, soda allum, or ammonium alum) and glucose. In certain embodiments, the compositions comprise an alum, glucose, and catalase. In certain embodiments, the compositions comprise an alum, glucose, and pyruvate. In certain embodiments, the compositions comprise an alum, glucose, and glutathione. In certain embodiments, the compositions comprise an alum, glucose, and a glutathione peroxidase. Each of the embodiments of this paragraph can further comprise one or more RNase inhibitors (e.g., any RNase inhibitor or combination thereof described or suggested herein) and/or biomolecules (e.g., any sample comprising biomolecules, such as a biological sample).

In certain embodiments, the compositions of the immediately foregoing paragraph further comprise EDTA. In certain embodiments, the compositions of the immediately foregoing paragraph further comprise EDTA and glycerol. In certain embodiments, the compositions of the immediately foregoing paragraph further comprise EDTA and trehalose. In certain embodiments, the compositions of the immediately foregoing paragraph further comprise EDTA and dextran. In certain embodiments, the compositions of the immediately foregoing paragraph further comprise EDTA and polyvinyl alcohol. In certain embodiments, the compositions of the immediately foregoing paragraph further comprise EGTA. In certain embodiments, the compositions of the immediately foregoing paragraph further comprise EGTA and glycerol. In certain embodiments, the compositions of the immediately foregoing paragraph further comprise EGTA and trehalose. In certain embodiments, the compositions of the immediately foregoing paragraph further comprise EGTA and dextran. In certain embodiments, the compositions of the immediately foregoing paragraph further comprise EGTA and polyvinyl alcohol. In certain embodiments, the compositions of the immediately foregoing paragraph further comprise o-phenanthroline. In certain embodiments, the compositions of the immediately foregoing paragraph further comprise o-phenanthroline and glycerol. In certain embodiments, the compositions of the immediately foregoing paragraph further comprise o-phenanthroline and trehalose. In certain embodiments, the compositions of the immediately foregoing paragraph further comprise o-phenanthroline and dextran. In certain embodiments, the compositions of the immediately foregoing paragraph further comprise o-phenanthroline and polyvinyl alcohol. In certain embodiments, the compositions of the immediately foregoing paragraph further comprise EDTA and citrate. In certain embodiments, the compositions of the immediately foregoing paragraph further comprise EDTA, citrate, and glycerol. In certain embodiments, the compositions of the immediately foregoing paragraph further comprise EDTA, citrate, and trehalose. In certain embodiments, the compositions of the immediately foregoing paragraph further comprise EDTA, citrate, and dextran. In certain embodiments, the compositions of the immediately foregoing paragraph further comprise EDTA, citrate, and polyvinyl alcohol. In certain embodiments, the compositions of the immediately foregoing paragraph further comprise EGTA and citrate. In certain embodiments, the compositions of the immediately foregoing paragraph further comprise EGTA, citrate, and glycerol. In certain embodiments, the compositions of the immediately foregoing paragraph further comprise EGTA, citrate, and trehalose. In certain embodiments, the compositions of the immediately foregoing paragraph further comprise EGTA, citrate, and dextran. In certain embodiments, the compositions of the immediately foregoing paragraph further comprise EGTA, citrate, and polyvinyl alcohol. In certain embodiments, the compositions of the immediately foregoing paragraph further comprise o-phenanthroline and citrate. In certain embodiments, the compositions of the immediately foregoing paragraph further comprise o-phenanthroline, citrate, and glycerol. In certain embodiments, the compositions of the immediately foregoing paragraph further comprise o-phenanthroline, citrate, and trehalose. In certain embodiments, the compositions of the immediately foregoing paragraph further comprise o-phenanthroline, citrate, and dextran. In certain embodiments, the compositions of the immediately foregoing paragraph further comprise o-phenanthroline, citrate, and polyvinyl alcohol.

In certain embodiments, the inorganic compounds of the foregoing compositions (e.g., boric acid, borate, phosphoric acid or salts thereof, vanadate salts, alums) are in an aqueous medium (e.g., either before or after being mixed with a sample) and have a concentration of about 5 mM to about 500 mM, about 5.5 mM to about 400 mM, about 6 mM to about 300 mM, about 6.5 mM to about 250 mM, about 7 mM to about 200 mM, about 7.5 mM to about 150 mM, about 8 mM to about 140 mM, about 8.5 mM to about 130 mM, about 9 mM to about 120 mM, about 9.5 mM to about 110 mM, about 10 mM to about 100 mM, about 10.1 mM to about 90 mM, about 10.2 mM to about 80 mM, about 10.3 mM to about 70 mM, about 10.4 mM to about 60 mM, about 10.5 mM to about 50 mM, about 10.6 mM to about 40 mM, about 10.7 mM to about 30 mM, about 10.8 mM to about 25 mM, about 10.9 mM to about 20 mM, about 11 mM to about 15 mM, or about 12.5 mM. In certain embodiments, the stabilizers of the foregoing compositions (e.g., dimethyl sulfoxide, histidine, mannitol, catalase, pyruvate, glutathione, and glutathione peroxidases) are in an aqueous medium (e.g., either before or after being mixed with a sample) and have a concentration of about 1.0 mM to about 250 mM, about 1.5 mM to about 200 mM, about 2.0 mM to about 150 mM, about 2.5 mM to about 100 mM, about 3.0 mM to about 75 mM, about 3.5 mM to about 50 mM, about 4.0 mM to about 40 mM, about 4.5 mM to about 30 mM, about 5.0 mM to about 20 mM, about 5.5 mM to about 10 mM, about 6.0 mM to about 7.5 mM, or about 6.25 mM.

In certain embodiments, the metal chelators of the foregoing compositions (e.g., EDTA, EGTA) are in an aqueous medium (e.g., either before or after being mixed with a sample) and have a concentration of about 0.01 mM to about 50 mM, about 0.02 mM to about 45 mM, about 0.03 mM to about 40 mM, about 0.04 mM to about 35 mM, about 0.05 mM to about 30 mM, about 0.06 mM to about 25 mM, about 0.07 mM to about 20 mM, about 0.08 to about 15 mM, about 0.09 mM to about 10 mM, about 0.1 mM to about 5 mM, or about 0.1 mM. In certain embodiments, the metal chelators of the foregoing compositions (e.g., citrate) are in an aqueous medium (e.g., either before or after being mixed with a sample) and have a concentration of about 0.01 mM to about 200 mM, about 0.02 mM to about 180 mM, about 0.03 mM to about 160 mM, about 0.04 mM to about 140 mM, about 0.05 mM to about 120 mM, about 0.06 mM to about 100 mM, about 0.07 mM to about 80 mM, about 0.08 to about 60 mM, about 0.09 mM to about 40 mM, about 0.1 mM to about 20 mM, about 0.1 mM to about 15 mM, about 0.1 mM to about 10 mM, about 0.2 mM to about 9 mM, about 0.3 mM to about 8 mM, about 0.4 mM to about 7 mM, about 0.5 mM to about 6 mM, about 0.6 mM to about 5 mM, about 0.7 mM to about 4 mM, about 0.8 mM to about 3 mM, about 0.9 mM to about 2 mM, about 1.0 mM to about 1.5 mM, or about 1.25 mM. In certain embodiments, the plasticizers of the foregoing compositions (e.g., glycerol, trehalose, dextran, and polyvinyl alcohol) are in an aqueous medium (e.g., either before or after being mixed with a sample) and have a concentration of about 0.01% to about 8.0%, about 0.02% to about 5.0%, about 0.03% to about 2.0%, about 0.04% to about 1.5%, about 0.05% to about 1%, or about 0.06% to about 0.5%.

In another aspect, the invention provides compositions comprising a stabilizer. The stabilizer can be any stabilizer disclosed or suggested herein (e.g., a singlet oxygen quencher, a hydroxyl radical scavenger, a hydroperoxide removing agent, a reducing agent, a metal chelator, a detergent, a chaotrope, or any combination thereof). In certain embodiments, the stabilizer is a singlet oxygen quencher. The singlet oxygen quencher can be any singlet oxygen quencher described or suggested herein. In other embodiments, the stabilizer is a hydroxyl radical scavenger. The hydroxyl radical scavenger can be any hydroxyl radical scavenger described or suggested herein. In still other embodiments, the stabilizer can be a hydroperoxide removing agent. The hydroperoxide removing agent can be any hydroperoxide removing agent described or suggested herein.

In certain embodiments, the compositions further comprise an inorganic salt, a plasticizer, or a combination thereof. The inorganic salt can be any inorganic salt disclosed or suggested herein. Thus, in certain embodiments, the compositions comprise a stabilizer and an inorganic salt. In certain embodiment, the inorganic salt comprises an element from the first Group (e.g., Group IA) of the Period Table of Elements. In certain embodiments, the inorganic salt is sodium chloride. In other embodiments, the inorganic salt is potassium chloride. In certain embodiments, the ratio of stabilizer (e.g., singlet oxygen quencher, hydroxyl radical scavenger, hydroperoxide removing agent) to inorganic salt is about 20:1 to about 1:20, about 15:1 to about 1:15, about 10:1 to about 1:10, about 7:1 to about 1:7, about 5:1 to about 1:5, about 4:1 to about 1:4, about 3:1 to about 1:3, about 2:1 to about 1:2, or about 1:1.

In certain embodiments, the compositions comprise a stabilizer and a plasticizer. The plasticizer can be any plasticizer described or suggested herein (e.g., a monosaccharide, disaccharide, complex sugar, long-chain poly-alcohol, or a short-chain poly-alcohol). In certain embodiments, the plasticizer is a linear or branched short-chain poly-alcohol (e.g., glycerol). In certain embodiments, the plasticizer is glycerol. In certain embodiments, the plasticizer is a monosaccharide (e.g., glucose). In other embodiments, the plasticizer is a disaccharide (e.g., sucrose, trehalose, or mannose). In other embodiments, the plasticizer is a complex sugar (e.g., ficol or dextran (e.g., short-chain dextran having a MW less than 10 kD)). In certain embodiments, the ratio of stabilizer to plasticizer is about 20:1 to about 1:20, about 15:1 to about 1:15, about 10:1 to about 1:10, about 7:1 to about 1:7, about 5:1 to about 1:5, about 4:1 to about 1:4, about 3:1 to about 1:3, about 2:1 to about 1:2.

In certain embodiments, the compositions further comprise one or more RNase inhibitors. Thus, in certain embodiments, the compositions comprise a stabilizer, either an inorganic salt or a plasticizer (or a combination thereof), and one or more RNase inhibitors. The RNase inhibitors can be any RNase inhibitors disclosed or suggested herein.

In certain embodiments, the compositions further comprise biomolecules. The biomolecules can be any biomolecules described or suggested herein. In certain embodiments, the ratio of stabilizer (e.g., singlet oxygen quencher, hydroxyl radical scavenger, hydroperoxide removing agent) to biomolecules in the composition is about 20000:1 to about 2:1, about 10000:1 to about 1000:1, about 1000:1 to about 100:1, about 100:1 to about 10:1, or about 10:1 to about 1:1. In other embodiments, the ratio of stabilizer (e.g., singlet oxygen quencher, hydroxyl radical scavenger, hydroperoxide removing agent) to biomolecules in the composition is about 5000:1 to about 50:1, about 1000:1 to about 10:1, about 500:1 to about 5:1, about 100:1 to about 2:1, about 50:1 to about 1:2. In still other embodiments, the ration of inorganic compound to biomolecules is about 50:1, about 40:1, about 30:1, about 20:1, about 10:1, or about 1:1 by weight.

In certain embodiments, the compositions comprise a singlet oxygen quencher (e.g., an alkyl imidazole) in combination with an inorganic salt, a plasticizer, or a combination thereof. The inorganic salt and the plasticizer can be any inorganic salt and plasticizer disclosed or suggested herein. In certain embodiments, the composition further comprises an additional stabilizer. For example, in certain embodiments, the additional stabilizer is a second singlet oxygen quencher (e.g., an indole or a sulfur-containing amino acid). In other embodiments, the additional stabilizer is a stabilizer other than a singlet oxygen quencher (e.g., a hydroxyl radical scavenger, a hydroperoxide removing agent, a metal chelator, or any combination thereof). The additional stabilizer can be any stabilizer disclosed herein. In certain embodiments, the composition further comprises one or more RNase inhibitors, biomolecules, or a combination thereof. The RNase inhibitors and biomolecules can be any RNase inhibitors and biomolecules disclosed herein.

In certain embodiments, the compositions comprise a hydroxyl radical scavenger in combination with an inorganic salt, a plasticizer, or a combination thereof. The inorganic salt and the plasticizer can be any inorganic salt and plasticizer disclosed or suggested herein. In certain embodiments, the composition further comprises an additional stabilizer. For example, in certain embodiments, the additional stabilizer is a second hydroxyl radical scavenger. In other embodiments, the additional stabilizer is a stabilizer other than a hydroxyl radical scavenger (e.g., a singlet oxygen quencher, a hydroperoxide removing agent, a metal chelator, or any combination thereof). The additional stabilizer can be any stabilizer disclosed herein. In certain embodiments, the composition further comprises one or more RNase inhibitors, biomolecules, or a combination thereof. The RNase inhibitors and biomolecules can be any RNase inhibitors and biomolecules disclosed herein.

In certain embodiments, the compositions comprise a hydroperoxide removing agent in combination with an inorganic salt, a plasticizer, or a combination thereof. The inorganic salt and the plasticizer can be any inorganic salt and plasticizer disclosed or suggested herein. In certain embodiments, the composition further comprises an additional stabilizer. For example, in certain embodiments, the additional stabilizer is a second hydroperoxide removing agent. In other embodiments, the additional stabilizer is a stabilizer other than a hydroperoxide removing agent (e.g., a singlet oxygen quencher, a hydroxyl radical scavenger, a metal chelator, or any combination thereof). The additional stabilizer can be any stabilizer disclosed herein. In certain embodiments, the composition further comprises one or more RNase inhibitors, biomolecules, or a combination thereof. The RNase inhibitors and biomolecules can be any RNase inhibitors and biomolecules disclosed herein.

In certain embodiments, the compositions comprise histidine and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise histidine, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise histidine, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise tryptophan and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise tryptophan, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise tryptophan, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise methionine and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise methionine, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise methionine, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise tyrosine and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise tyrosine, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise tyrosine, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise ascorbate and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ascorbate, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise ascorbate, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise azide and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise azide, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise azide, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise tocopherol and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise tocopherol, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise tocopherol, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise carotene and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise carotene, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise carotene, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise DMSO and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise DMSO, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise DMSO, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise mannitol and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise mannitol, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise mannitol, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise catalase and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise catalase, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise catalase, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise pyruvate and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise pyruvate, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise pyruvate, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the compositions comprise glutathione and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise glutathione, sodium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. In certain embodiments, the compositions comprise glutathione, potassium chloride and, optionally, and a plasticizer selected from the group consisting of ethylene glycol, 1,3-propane diol, glycerol, erythritol, glucose, sucrose, trehalose, mannose, dextran, polyvinyl alcohol and polyserine. Each of the embodiments of this paragraph can further comprise one or more metal chelators (e.g., EDTA, EGTA, o-phenanthroline, and/or citrate), one or more RNase inhibitors (e.g., any RNase inhibitor or combination thereof described or suggested herein), biomolecules (e.g., any sample comprising biomolecules, such as a biological sample), or any combination thereof.

In certain embodiments, the stabilizer (e.g., singlet oxygen quencher, hydroxyl radical scavenger, hydroperoxide removing agent) is the principal component of the composition. In certain embodiments, the stabilizer constitutes at least 5%, 10%, 15%, 20%, 25%, 30%, 35%, 40%, 45%, or more of the composition. In other embodiments, the stabilizer (e.g., singlet oxygen quencher, hydroxyl radical scavenger, hydroperoxide removing agent) is the principal non-water component of the composition. In certain embodiments, the stabilizer constitutes at least 5%, 10%, 15%, 20%, 25%, 30%, 35%, 40%, 45%, or more of the non-water portion of the composition.

In certain embodiments, the stabilizer (e.g., singlet oxygen quencher, hydroxyl radical scavenger, hydroperoxide removing agent) is part of an aqueous medium of the invention (e.g., either before or after being mixed with a sample) and is present at a concentration of about 0.05 mg/ml to about 100.0 mg/ml, about 0.1 mg/ml to about 75.0 mg/ml, about 0.2 mg/ml to about 50.0 mg/ml, about 0.3 mg/ml to about 25.0 mg/ml, about 0.4 mg/ml to about 15.0 mg/ml, or about 0.5 mg/ml to about 10.0 mg/ml. In certain embodiments, the stabilizer (e.g., singlet oxygen quencher, hydroxyl radical scavenger, hydroperoxide removing agent) is part of an aqueous medium of the invention (e.g., either before or after being mixed with a sample) and is present at a concentration of about 1.0 mM to about 500 mM, about 2.0 mM to about 400 mM, about 3.0 mM to about 300 mM, about 4.0 mM to about 200 mM, about 5.0 mM to about 100 mM, about 6.0 mM to about 95 mM, about 7.0 mM to about 90 mM, about 8.0 mM to about 85 mM, about 9.0 mM to about 80 mM, about 10 mM to about 75 mM, about 11 mM to about 70 mM, about 12 mM to about 65 mM, about 13 mM to about 60 mM, about 14 mM to about 55 mM, about 15 mM to about 50 mM, about 20 mM to about 40 mM, or about 30 mM. In certain embodiments, the stabilizer (e.g., singlet oxygen quencher, hydroxyl radical scavenger, hydroperoxide removing agent) is part of an aqueous medium of the invention (e.g., either before or after being mixed with a sample) and is present at a concentration of about 1.0 mM to about 50 mM, about 2.0 mM to about 40 mM, about 3.0 mM to about 30 mM, about 4.0 mM to about 20 mM, about 5.0 mM to about 10 mM, or about 6.25 mM.

In certain embodiments, the inorganic salt (e.g., sodium chloride or potassium chloride) is part of an aqueous medium of the invention (e.g., either before or after being mixed with a sample) and is present at a concentration of about 0.05 mg/ml to about 100.0 mg/ml, about 0.1 mg/ml to about 75.0 mg/ml, about 0.2 mg/ml to about 50.0 mg/ml, about 0.3 mg/ml to about 25.0 mg/ml, about 0.4 mg/ml to about 15.0 mg/ml, or about 0.5 mg/ml to about 10.0 mg/ml. In certain embodiments, the inorganic salt (e.g., sodium chloride or potassium chloride) is part of an aqueous medium of the invention (e.g., either before or after being mixed with a sample) and is present at a concentration of about 1.0 mM to about 500 mM, about 2.0 mM to about 450 mM, about 3.0 mM to about 400 mM, about 4.0 mM to about 350 mM, about 5.0 mM to about 300 mM, about 6.0 mM to about 250 mM, about 7.0 mM to about 200 mM, about 8.0 mM to about 150 mM, about 9.0 mM to about 125 mM, about 10 mM to about 100 mM, about 11 mM to about 90 mM, about 12 mM to about 80 mM, about 13 mM to about 70 mM, about 14 mM to about 60 mM, about 15 mM to about 50 mM, about 20 mM to about 40 mM, or about 30 mM. In certain embodiments, the inorganic salt (e.g., sodium chloride or potassium chloride) is part of an aqueous medium of the invention (e.g., either before or after being mixed with a sample) and is present at a concentration of about 1.0 mM to about 50 mM, about 2.0 mM to about 40 mM, about 3.0 mM to about 30 mM, about 4.0 mM to about 20 mM, about 5.0 mM to about 10 mM, or about 6.25 mM.

In certain embodiments, the plasticizer is the principal component of the composition. In certain embodiments, the plasticizer constitutes at least 5%, 10%, 15%, 20%, 25%, 30%, 35%, 40%, 45%, or more of the composition. In other embodiments, the plasticizer is the principal non-water component of the composition. In certain embodiments, the plasticizer constitutes at least 5%, 10%, 15%, 20%, 25%, 30%, 35%, 40%, 45%, or more of the non-water portion of the composition.

In certain embodiments, the plasticizers of the foregoing compositions (e.g., glycerol, trehalose, dextran, and polyvinyl alcohol) are in an aqueous medium (e.g., either before or after being mixed with a sample) and have a concentration of about 0.01% to about 8.0%, about 0.02% to about 5.0%, about 0.03% to about 2.0%, about 0.04% to about 1.5%, about 0.05% to about 1%, or about 0.06% to about 0.5%.

In another aspect, the invention provides compositions comprising at least three components selected from the list consisting of an inorganic compound, a singlet oxygen quencher, a hydroxyl radical scavenger, a hydroperoxide removing agent, a reducing agent, a metal chelator, a detergent, and a plasticizer. The inorganic compound, singlet oxygen quencher, hydroxyl radical scavenger, hydroperoxide removing agent, reducing agent, metal chelator, detergent, and plasticizer can be any inorganic compound, singlet oxygen quencher, hydroxyl radical scavenger, hydroperoxide removing agent, reducing agent, metal chelator, detergent, and plasticizer described or suggested herein. In certain embodiments, the compositions comprise at least three components selected from the list consisting of an inorganic compound, a singlet oxygen quencher, a hydroyl radical scavenger, a hydroperoxide removing agent, and a metal chelator.

In certain embodiments, the compositions comprise an inorganic compound, a hydroxyl radical scavenger, and a hydroperoxide removing agent. In other embodiments, the compositions comprise an inorganic compound, a singlet oxygen quencher, and a hydroxyl radical scavenger. In other embodiments, the compositions comprise an inorganic compound, a singlet oxygen quencher, and a hydroperoxide removing agent. In other embodiments, the compositions comprise a singlet oxygen quencher, a hydroxyl radical scavenger, and a hydroperoxide removing agent. In certain related embodiments, the compositions further comprise a metal chelator, a plasticizer, one or more RNase inhibitors, or any combination thereof.

In certain embodiments, the compositions further comprise biomolecules (e.g., a sample, such as a biological sample, comprising biomolecules).

The compositions of the present invention can be provided in any form suitable for biomolecule storage. In one embodiment, a composition of the present invention is provided as a solid-state matrix. As used herein, "solid-state" means that the matrix is provided in a solid or dry form which can be converted to a liquid form by suspending, re-hydrating, or solubilizing the matrix in water. In certain embodiments, the solid-state matrix is obtained by air drying (e.g., in a chemical fume hood). In other embodiments, the solid state storage matrix is obtained by drying in a vacuum (e.g., in a vacuum centrifuge). In certain embodiments, the solid-state matrix has a crystalline or paracrystalline structure. In certain embodiments, the solid-state matrix does not have a glass structure. In certain embodiments, the solid-state matrix has been equilibrated with atmospheric relative humidity and has a water content of 70%, 60%, 55%, 50%, 48%, 46%, 44%, 42%, 40%, 38%, 36%, 35%, 34%, 33%, 32%, 31%, 30%, or less by weight.

In other embodiments, a composition of the present invention is provided as an aqueous medium. As used herein, "aqueous" refers to a solution in which water is the principal solvent. The aqueous medium can be the form the composition has prior to being mixed with sample. Alternatively, the aqueous medium can be the result of mixing a dry-state matrix with a liquid sample. In preferred embodiments, an aqueous medium of the invention can be dried down (e.g., by air or vacuum drying) to obtain a solid state matrix of the invention. In certain embodiments, the aqueous medium, upon drying, forms a solid state matrix having a crystalline or paracrystalline structure. In certain embodiments, the aqueous medium, upon drying, does not form a glass structure. In other embodiments, a solid state matrix of the invention can be solubilized in water or a liquid biological sample (e.g., a bodily fluid, a tissue homogenate, a cellular lysate, a purified or synthetic sample of biomolecules), diluted or otherwise, to produce an aqueous medium of the invention.

In certain embodiments, the compositions of the invention do not comprise Tris base, EDTA, EGTA, or a combination thereof.

In certain embodiments, the compositions are substantially free of magnesium, chromium, manganese, iron, cobalt, nickel, copper, zinc, or lead. In this context, the term "substantially free" means that the composition is less than 0.5% magnesium, chromium, manganese, iron, cobalt, nickel, copper, zinc, or lead by weight, wherein the percentage is determined by dividing (1) the weight of magnesium, chromium, manganese, iron, cobalt, nickel, copper, zinc, or lead in the composition by (2) the weight of all non-water compounds in the composition and multiplying the result by 100. In preferred embodiments, the composition contains less than 0.1%, 0.05%, 0.01%, 0.005%, or less magnesium, chromium, manganese, iron, cobalt, nickel, copper, zinc, or lead.

In certain embodiments, the compositions are substantially free of one or more water soluble organic polymers, such as polyvinyl alcohol, dextran, dextran sulfate, and cellulose. In this context, "substantially free" means that the composition is less than 0.5% by weight of a particular water soluble organic polymers, where the percentage is determined by dividing (1) the weight of the water soluble organic polymer in the composition by (2) the weight of all non-water compounds in the composition and multiplying the result by 100. In certain embodiments, the composition contains less than 0.1%, 0.05%, 0.01%, 0.005%, of a particular water soluble organic polymer.

In certain embodiments, the compositions are inert with respect to one or more downstream methods that may be used to analyze biomolecules that have been stored in and/or stabilized by the compositions. The term "inert," as used herein in this context, means that the presence of a composition in a sample does not reduce the rate of the method by more than 50% and does significantly reduce the fidelity of the method. In certain embodiments, the composition is inert with respect to a method selected from the group consisting of nucleic acid transcription and/or amplification (e.g., reverse transcription, PCR, real time PCR, etc.), endonuclease digestion (e.g., reactions involving type II endonucleases, such as EcoRI, BamHI, Hindiii, NotI, SmaI, BglII, etc.), cloning techniques (e.g., ligation), protein digestion (e.g., reactions involving proteinases such as proteinase K, trypsin, chymotrypsin, savinase, etc.), microarray analysis (e.g., of nucleic acids or proteins), immunoassays (e.g., immunoprecipitation, ELISA, etc.), mass spectroscopy, or any combination thereof. In certain embodiments, the composition is inert upon dilution (e.g., dilution by a factor of 2, 3, 4, 5, 6, 7, 8, 9, 10, 15, 20, or more). In other embodiments, the composition is inert in undiluted form.

Sample Carriers

In another aspect, the invention provides sample carriers comprising compositions of the invention. In certain embodiments, the sample carriers comprise a container and a sample node, wherein the sample node comprises or consists of a composition disclosed herein (e.g., a solid-state matrix or an aqueous medium disclosed herein). In certain embodiments, the sample node is reversibly attached to the container. In certain embodiments, the container contains and/or supports the sample node. The container can be any size and shape suitable for containing or supporting such compositions and/or practicing the methods of the invention. For example, in certain embodiments, the container is a tube (e.g., a test tube, a sample tube having a volume of about 0.1 ml to about 2.0 ml, etc.) or a well (e.g., a well in a plate, such as a standard multi-well plate).

In certain embodiments, the container has a volume of about 10). 11 to about 2 ml, about 25 µl to about 1.5 ml, about 50 µl to about 1000 µl, about 75 µl to about 800 µl, about 100 µl to about 700 µl, about 125 µl to about 600 µl, or about 150 µl to about 500 µl.

In certain embodiments, the sample carrier comprises an identifying indicia, such as an optical barcode. In certain embodiments, the container comprises an identifying indicia. For example, in certain embodiments, the container comprises an optical barcode or a biological barcode. Biological barcodes have been described, for example, in US Patent Application No. 2004/0219533 and No. 2005/0026181. In certain embodiments, the sample node comprises an identifying indicia, such as a biological barcode.

In certain embodiments, the sample node comprises about 10 µg to about 1000 µg, about 15 µg to about 900 µg, about 20 µg to about 800 µg, about 25 µg to about 700 µg, about 30 µg to about 600 µg, about 35 µg to about 500 µg, about 40 µg to about 400 µg, about 45 µg to about 300 µg, about 50 µg to about 200 µg, about 55 µg to about 150 µg, about 60 µg to about 125 µg, about 65 µg to about 100 µg, or about 70 µg to about 80 µg of a solid state matrix disclosed herein. In other embodiments, the sample node comprises about 1.0 mg to about 100 mg, about 2.0 mg to about 90 mg, about 3.0 mg to about 80 mg, about 4.0 mg to about 70 mg, about 5.0 mg to about 60 mg, about 6.0 mg to about 50 mg, about 7.0 mg to about 40 mg, about 8.0 mg to about 30 mg, about 9.0 mg to about 20 mg, or about 10 mg of a solid state matrix disclosed herein. In other embodiments, the sample node comprises about 10 µl to about 1000 µl, about 15 µl to about 900 µl, about 20 µl to about 800 µl, about 25 µl to about 700 µl, about 30 µl to about 600 µl, about 35 µl to about 500 µl, about 40 µl to about 400 µl, about 45 µl to about 300 µl, about 50 µl to about 200 µl, about 55 µl to about 150 µl, about 60 µl to about 125 µl, about 65 µl to about 100 µl, or about 70 µl to about 90 µl of an aqueous medium disclosed herein.

In certain embodiments, the sample carrier comprises a plurality of containers and a plurality of discrete sample nodes. As used herein in this context, "discrete" means that the sample nodes are physically separate from the other sample nodes of the sample carrier and can be accessed and manipulated individually. Thus, for example, each of the plurality of sample nodes can be individually contained or supported by a single container. In certain embodiments, the plurality of containers is a plurality of tubes (e.g., an 8×12 array of screw cap tubes having an SBS microtiter footprint). In certain embodiments, the plurality of containers is a plurality of wells in a multi-well plate (e.g., a microtiter plate having an SBS microtiter footprint). In general, such multi-compartment container is compatible with automation and robotic handling.

In certain embodiments, each of said plurality of containers comprises an identifying indicia. For example, in certain embodiments, each of said plurality of containers comprises an optical barcode or a biological barcode. In other embodiments, each of said plurality of containers can be identified by its position within the sample carrier (e.g., the coordinates of a well within a multi-well plate).

In certain embodiments, the sample carrier further comprises biomolecules. Thus, in certain embodiments, the sample carrier comprises one or more samples, such as biological samples, containing biomolecules. The samples can be any biological sample disclosed herein, such as a bodily fluid, a tissue homogenate, a cell lysate, a fraction thereof, a purified sample, or a synthetic sample.

In another aspect, the invention provides kits comprising a composition disclosed herein and an instruction for using the composition for storage of biomolecules. In certain embodiments, the composition is a solid-state matrix disclosed herein. In other embodiments, the composition is an aqueous medium disclosed herein. In certain embodiments, the instruction describes a method for dry storage of biomolecules disclosed herein. In other embodiments, the instruction described a method for stabilizing biomolecules (e.g., in a dry state or in a liquid medium). In still other embodiments, the instruction describes a method for shipping biomolecules (e.g., in a dry state) described herein.

In certain embodiments, the kits include a container that contains the composition. The container can be any size or shape suitable for containing the composition. In certain embodiments, the container is a bottle. In certain embodiments, the container contains a composition disclosed herein (e.g., an aqueous medium or a dry-state matrix) in sufficient quantity to provide storage and/or stability to a plurality of samples (e.g., 10, 20, 30, 40, 50, 75, 100, 150, 200, or more samples). In certain embodiments, the container contains 100 µl, 200 µl, 300 µl, 400 µl, 500 µl, 750 µl, 1.0 ml, 1.5 ml, 2.0 ml, 2.5 ml, 5.0 ml, 7.5 ml, 10.0 ml, 15.0 ml, 20.0 ml, or more of an aqueous medium of the invention. In other embodiments, the container contains 500 µg, 1 mg, 1.5 mg, 2.0 mg, 2.5 mg, 5.0 mg, 7.5 mg, 10.0 mg, 15.0 mg, 20.0 mg, 50.0 mg, 100 mg, 250 mg, 500 mg, 1 g, or more of a dry-state matrix of the invention.

In other embodiments, the kits includes a sample carrier disclosed herein. For example, in certain embodiments, the kit includes a sample carrier comprising a plurality of containers (e.g., a multi-well plate), wherein each of said plurality of wells contains a storage composition disclosed herein.

Methods

In another aspect, the invention provides methods of storing biomolecules. In certain embodiments, the methods comprise mixing a sample that contains biomolecules, such as a biological sample, with a composition described herein (e.g., a solid state matrix or an aqueous medium described herein) to form a mixture, and drying down the mixture to form a dry-state matrix comprising biomolecules. The sample can be any type of sample described herein.

In certain embodiments, the sample is a liquid sample, such as a bodily fluid (e.g., blood, serum, sputum, urine, cerbrospinal fluid, etc.), a cellular lysate, or a tissue homogenate. In certain embodiments, the sample is a liquid sample and is mixed with a dry-state matrix of the invention. In other embodiments, the sample is a liquid sample and is mixed with an aqueous medium of the invention. In other embodiments, the sample is carried by a solid support, such as a cotton swab, a filter paper, or a sponge. For example, in certain embodiments, the sample is a liquid sample and the mixing comprising washing the solid support with an aqueous medium of the invention. In still other embodiments, the sample is a solid sample, such as a piece of tissue (e.g., a biopsy). For example, in certain embodiments, the sample is a solid sample and is stored in an aqueous medium for storage (e.g., overnight, or for 1, 2, 3, 4, 5, 6, 7 days or more). In certain embodiments, a solid sample is placed in a mixture of an aqueous medium of the invention and another liquid known for stabilizing biomolecules present in a solid tissue sample such as a biopsy. For example, in certain embodiments, the sample is placed in a mixture of an aqueous medium of the invention and RNALater™ (by Ambion) or Allprotect™ (by Qiagen).

In certain embodiments, mixing the sample with a composition of the invention comprises agitating (e.g., by repeat pipetting, shaking, or vortexing) the combination of sample and composition. In other embodiments, mixing the sample with a composition of the invention comprises incubating the combination of sample and composition at a temperature above room temperature (e.g., at a temperature of 30° C., 37° C., 40° C., 42° C., 45° C., 50° C., 55° C., 60° C., or higher). In certain embodiments, mixing the sample with a composition of the invention comprises incubating the combination of sample and composition at a temperature less than 70° C., 65° C., 60° C., 55° C., 50° C., 45° C., 40° C., or lower. In certain embodiments, mixing the sample with a composition of the invention comprises agitating the combination of sample and composition, and incubating the combination at a temperature between room temperature and 60° C. As used herein, "room temperature" is the temperature in a typical laboratory. Thus, in general, room temperature is between about 20° C. and about 28° C., or between about 22° C. and about 26° C.

In certain embodiments, drying down the storage solution comprises air drying (e.g., air drying in a chemical fume hood overnight). In other embodiments, drying down the storage solution comprises vacuum drying (e.g., drying in a vacuum centrifuge for one or more hours). Following drying, the dry-state matrix can be stored, for example, in a sample archive. Suitable archives have been described, e.g., in U.S. Pat. No. 7,142,987 and U.S. Patent Application No. 2003/0129755.

In certain embodiments, the storage is short term (e.g., the time it takes to transport the biomolecules to a remote location for further processing). Thus, for example, in certain embodiments, the storage is for 2, 4, 6, 8, 10, 12, 14, 16, 18, 20, 22 24, or more hours, or for 1, 2, 3, 4, 5, 6, 7 or more days. In certain embodiments, the storage is for an intermediate time period (e.g., for 1, 2, 3, 4, 5, 6, 7, 8, 9, 10, or more weeks, or for 1, 2, 3, 4, 5, 6, 7, 8, 9, 10, 11, 12, 13, 14, 15, 16, 17, 18, or more months). In still other embodiments, the storage is long term (e.g., for archiving). Thus, for example, in certain embodiments, the storage is for 1, 2, 3, 4, 5, 6, 7, 8, 9, 10, 11, 12, 15, 20, or more years.

In general, the compositions of the present invention can be used to store any biomolecule. Exemplary biomolecules include without any limitation, DNA, RNA, nucleic acid, polynucleotide, oligonucleotide, amino acid, peptide, polypeptide. Such biomolecules can be in any form, e.g., in a biological sample, an extract, any other intermediate or semi-processed biological samples, a purified sample, or a synthetic sample. Exemplary biological samples include without any limitation, blood, plasma, urine, saliva, cerebrospinal fluid, or any biological fluid, skin cells, cell or tissue samples, cell lysate, nuclear extract, nucleic acid extract, protein extract, cytoplasmic extract, etc.

In a related aspect, the invention provides methods of transporting biomolecules. In certain embodiments, the methods comprise storing the biomolecules in a dry-state matrix of the invention (e.g., according to a method of storing biomolecules described herein). Thus, for example, in certain embodiments the methods comprise mixing a sample that contains biomolecules, such as a biological sample, with a composition described herein (e.g., a solid-state matrix or an aqueous medium described herein) to form a mixture, drying down the mixture to form a dry-state matrix comprising biomolecules, and transporting the dry-state matrix comprising biomolecules. The sample can be any type of sample described herein.

In certain embodiments, the dry-state matrix comprising biomolecules is transported to a location where the biomolecules can be stored for future use (e.g., an archive). In other embodiments, the dry-state matrix comprising biomolecules is transported to a location where the biomolecules can be analyzed (e.g., a laboratory). In certain embodiments, the dry-state matrix comprising biomolecules is transported at a temperature greater than 25° C. In other embodiments, the dry-state matrix comprising biomolecules is transported at a temperature greater than 37° C. In still other embodiments, the dry-state matrix comprising biomolecules is transported at a temperature greater than 50° C. Thus, for example, in certain embodiments, the dry-state matrix comprising biomolecules is exposed to ambient temperatures of about 25° C. to about 80° C., about 37° C. to about 75° C., or about 50° C. to about 70° C. during said transporting step.

In certain embodiments, the dry-state matrix comprising biomolecules is exposed to elevated temperatures for one or more hours (e.g., for 1, 2, 3, 4, 5, 6, 7, 8, 9, 10, 12, 14, 16, 18, 20, 22, or 24 hours, or more) during said transporting. As used herein in this context, "elevated temperatures" refers to temperatures greater than 25° C. Thus, for example, in certain embodiments the dry-state matrix comprising biomolecules is exposed to temperatures greater than 25° C., greater than 37° C., greater than 50° C., and/or greater than 70° C. for one or more hours (e.g., for 1, 2, 3, 4, 5, 6, 7, 8, 9, 10, 12, 14, 16, 18, 20, 22, or 24 hours, or more). In certain embodiments, the biomolecules in the dry-state matrix are not damaged by the exposure to elevated temperatures. For example, in certain embodiments, greater that 50%, 60%, 70%, 80%, 90%, or more of a particular type of biomolecule (e.g., DNA, RNA, protein, etc.) will remain in good condition for analysis following the exposure to elevated temperatures.

In certain embodiments, the transporting occurs by air (e.g., in an airplane). In certain embodiments, the transporting occurs by ground (e.g., in a delivery vehicle).

In another aspect, the invention provides a method of stabilizing biomolecules. In certain embodiments, the method comprises mixing a sample comprising biomolecules with a composition described herein (e.g., a dry-state matrix or an aqueous medium described herein) to form a mixture, wherein at least one biomolecule in the mixture is stabilized by the presence of the composition. As used herein, a biomolecule is "stabilized" by a composition when there is a lower likelihood that is will become degraded over time in the presence of the composition as compared to in the absence of the composition. In certain embodiments, the stabilization occurs in solution. Thus, for example, the invention provides a method of stabilizing biomolecules in solution, the method comprising mixing a sample comprising biomolecules with an aqueous medium described herein, wherein the at least one biomolecule is stabilized by the aqueous medium. In other embodiments, the method comprises mixing a liquid sample comprising biomolecules with a dry-state matrix described herein, and resuspending the dry-state matrix in the liquid sample to form a mixture, wherein at least one biomolecule in the mixture is stabilized by the resuspended matrix.

In certain embodiments, the mixture is maintained at a temperature greater than 0° C. As used herein in this context, the term "maintained" simply means that the mixture is allowed to stand in a particular location characterized by a particular ambient temperature. Thus, for example, after a sample has been mixed with a composition of the invention, if the resulting mixture is set aside (e.g., while other samples are attended to), the sample is being maintained at the ambient temperature in the room where the mixture is located. In certain embodiments, the mixture is maintained at a temperature greater than 4° C., 10° C., 15° C., 20° C., 25° C., 30° C., 35° C., 37° C., or more. In certain embodiments, the biomolecules are maintained at a particular temperature (e.g., 25° C. or greater) for 5, 10, 15, 20, 25, 30, 35, 40, 45, 50, 55, 60, 75, 90, 105, 120, or more minutes. In certain embodiments, the biomolecules are maintained at a particular temperature (e.g., 25° C. or greater) for 1, 2, 3, 4, 5, 6, 7, 8, 9, 10, 12, 18, 24, 30, 36, 42, 48, or more hours. In certain embodiments, the biomolecules are maintained at a particular temperature (e.g., 25° C. or greater) for 1, 2, 3, 4, 5, 6, 7, 8, 9, 10, 11, 12, 13, 14, or more days.

In certain embodiments, the biomolecules stabilized are nucleic acids (e.g., DNA and/or RNA). In other embodiments, the biomolecules stabilized are proteins or peptides. In other embodiments, the biomolecules stabilized are carbohydrates. In other embodiments, the biomolecules stabilized are lipids. In still other embodiments, the molecules stabilized are small molecules, such as steroids, pharmaceutical drugs, and metabolites thereof.

In another aspect, the invention provides methods of recovering biomolecules. In certain embodiments, the methods comprise adding a resuspension fluid to a dry-state matrix of the present invention that comprises biomolecules, and resuspending the matrix. In certain embodiments, the volume of resuspension fluid added to the storage matrix is greater than the volume of storage solution that was dried down to form the storage matrix. For example, in certain embodiments, the volume of resuspension fluid added to the storage matrix is greater than the volume of storage solution by a factor of 1.25, 1.5, 1.75, 2.0, or more. In other embodiments, the volume of resuspension fluid added to the storage matrix is less than the volume of storage solution that was dried down to form the storage matrix. For example, in certain embodiments, the volume of resuspension fluid added to the storage matrix is less than the volume of storage solution by a factor of 1.25, 1.5, 1.75, 2.0, or more. In preferred embodiments, the volume of resuspension fluid added to the storage matrix is about the same as the volume of storage solution that was dried down to form the storage matrix.

In certain embodiments, the resuspension fluid is water. In other embodiments, the resuspension fluid is a buffer. For example, in certain embodiments, the resuspension fluid is a buffer that comprises Tris base (e.g., 10 mM Tris or TE). In certain embodiments, the resuspension fluid has a pH of about 7.0. For example, in certain embodiments, the resuspension fluid has a pH of about 5.5 to about 8.5, or about to about 8.0, or about 6.5 to about 7.5, or about 7.0.

Biomolecules recovered from dry-state matrices of the invention can be analyzed and manipulated using standard molecular and biochemical techniques. For example, recovered nucleic acid molecules can be amplified (e.g., using standard PCR or real-time PCR) and/or analyzed (e.g., using restriction endonucleases and other nucleic acid modification enzymes, as well as by hybridization, such as to microarrays or blots). In preferred embodiments, the recovered biomolecules do not require any purification prior to such manipulation and/or analysis.

EXAMPLES

The following examples are intended to illustrate, but not to limit, the invention in any manner, shape, or form, either explicitly or implicitly. While they are typical of those that might be used, other procedures, methodologies, or techniques known to those skilled in the art may alternatively be used.

Example 1

Boric Acid Dry-State Matrices

Matrices comprising a water-soluble inorganic compound, were fabricated in conical bottom, polypropylene, 96-well microtiter plates. 20 µL aliquots of medium consisting of a 4.0 mg/ml aqueous solution of boric acid were added to individual wells. The medium was subsequently air dried at room temperature onto the bottom surface of each well to form a discrete, solid-state inorganic matrix (i.e., a discrete sample node). The drying process typically required 2 hours in a vacuum centrifuge or overnight in a hood. FIG. 1 shows representative matrices formed according to these procedures.

Example 2

Boric Acid Plus Histidine Dry-State Matrices

Matrices comprising a water-soluble inorganic compound (boric acid) and a small-molecule stabilizer (histidine) were fabricated in a conical bottom, polypropylene, 96 well microtiter plate. 20 µL aliquots of medium consisting of an aqueous solution of boric acid (4.0 mg/ml) and histidine (from 0.5 mg/ml to 2.5 mg/ml) were added to individual wells. The medium was subsequently air dried at room temperature onto the bottom surface of each well to form a discrete, solid-state inorganic matrix (i.e., a discrete sample node). The drying process typically required 2 hours in a vacuum centrifuge or overnight in a hood.

Example 3

Boric Acid Plus Glycerol Dry-State Matrices

Matrices comprising a water-soluble inorganic compound (boric acid) and a plasticizer (glycerol) were fabricated in a conical bottom, polypropylene, 96 well microtiter plate. 20 µL aliquots of medium consisting of an aqueous solution of boric acid (4.0 mg/ml) and glycerol (from 0.5 mg/ml to 4.0 mg/ml) were added to individual wells. The medium was subsequently air dried at room temperature onto the bottom surface of each well to form a discrete, solid-state inorganic matrix (i.e., a discrete sample node). The drying process typically required 2 hours in a vacuum centrifuge or overnight in a hood.

Example 4

Storage of DNA in Dry-State Matrices Comprising Boric Acid with or without Histidine To the matrices described in Examples 1-2, 20 µL aliquots of human DNA (supplied by Roche) in TE buffer were added per well. The solid-state matrix in each well was resuspended and solubilized in the DNA solution by repeat pipetting. The resulting solutions were then air-dried to form solid-state matrices comprising biomolecules. The amount of DNA added to each well ranged from about 100 ng to about 5000 ng. After the matrices comprising DNA were formed, the plates were stored at room temperature (i.e., about 25° C.), 37° C., 55° C., or 76° C.

Example 5

Recovery of DNA from Dry-State Matrices by Addition of Water

To retrieve the DNA from the dry-state storage of Example 4, 20 µL of water was added to each well and the plates were incubated at room temperature for about 15 minutes. The DNA-containing solutions were retrieved by pipetting and then used "as is" or diluted with water as needed for further analysis.

Example 6

Gel Electrophoresis of DNA Recovered from Dry-State Matrices

Figure 2A:
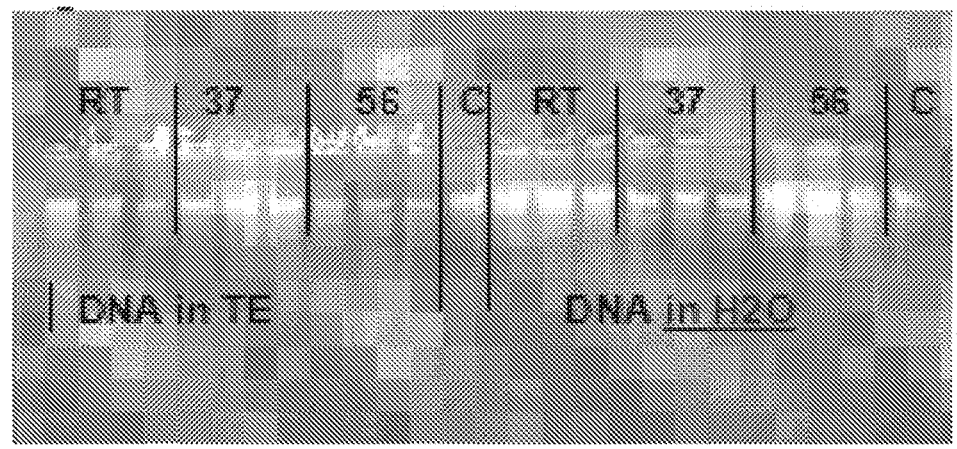
FIG. 2(a) is a picture of a gel showing ~100 ng of DNA recovered from 1 μg DNA samples following dry-state storage at room temperature (RT), 37° C., and 56° C., in a matrix composed of boric acid.
Figure 2B:
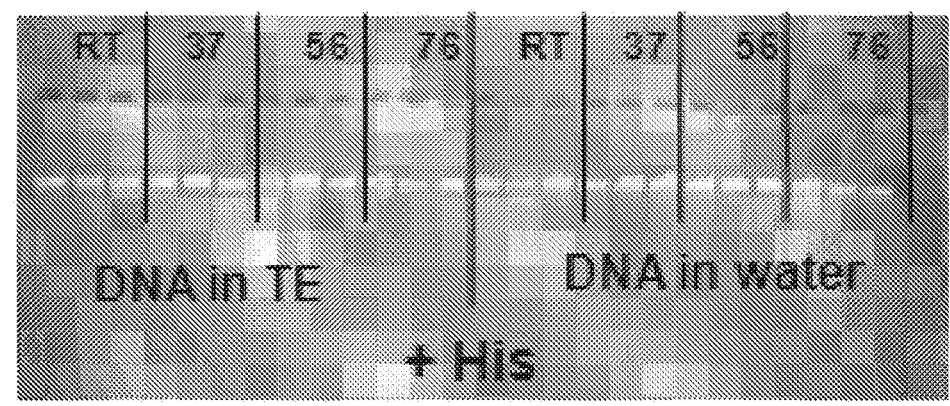
FIG. 2(b) is a picture of a gel showing ~100 ng of DNA recovered from 1 μg DNA samples following dry-state storage at RT, 37° C., 56° C., and 76° C., in a matrix composed of boric acid and histidine. Prior to dry-state storage, the DNA samples were maintained in solution in water or TE buffer.

DNA stored according to Example 4 and recovered according to Example 5 was analyzed by gel electrophoresis. A volume of DNA-containing solution corresponding to 100 ng of recovered DNA (assuming 100% recovery) was run on a 0.8% agarose gel at 250 volts for 1 hour and stained with Ethidium bromide. The results are shown in FIG. 2.

Example 7

Real Time PCR Analysis of Human DNA Recovered from Dry-State Matrices

Real time PCR was used to compare and evaluate the recovery of DNA from the dry-state matrices of Example 4. The DNA was recovered as described in Example 5. PCR analysis was based on a nuclear chromosome encoded gene, -actin, as provided by ABI (Cat#401846)

Figure 3A:
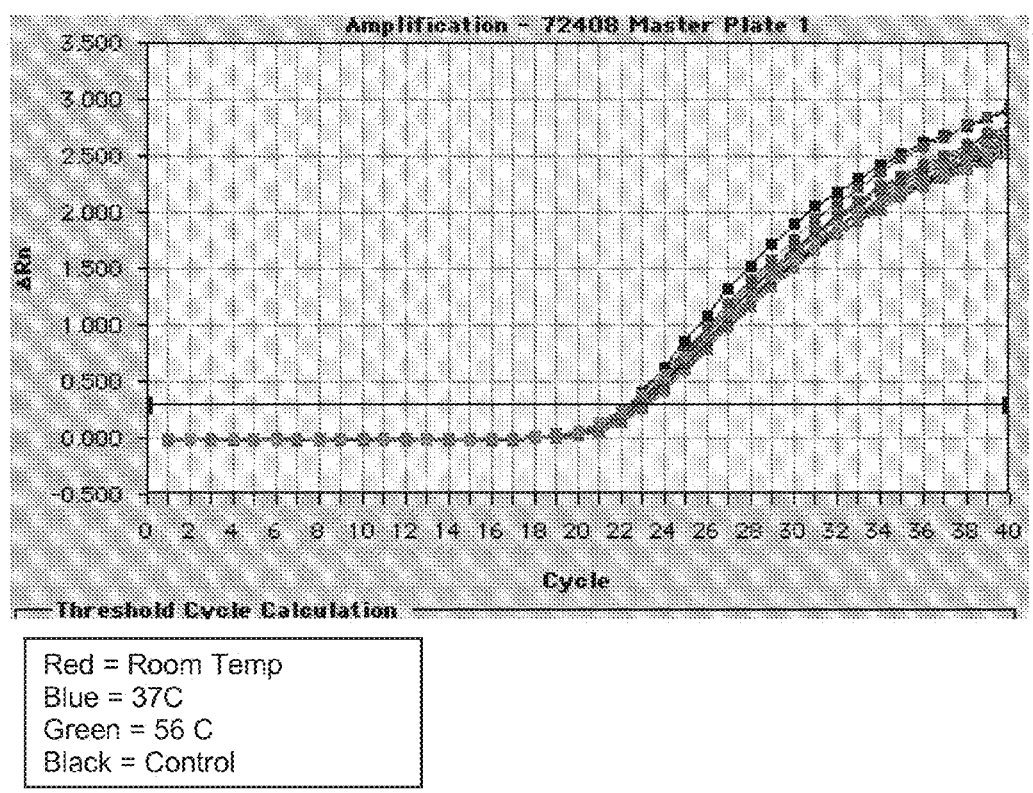
FIG. 3(a) shows real time PCR results for DNA recovered from 250 ng DNA samples following dry-state storage at room temperature, 37° C., and 56° C., in a matrix composed of boric acid.
Figure 3B:
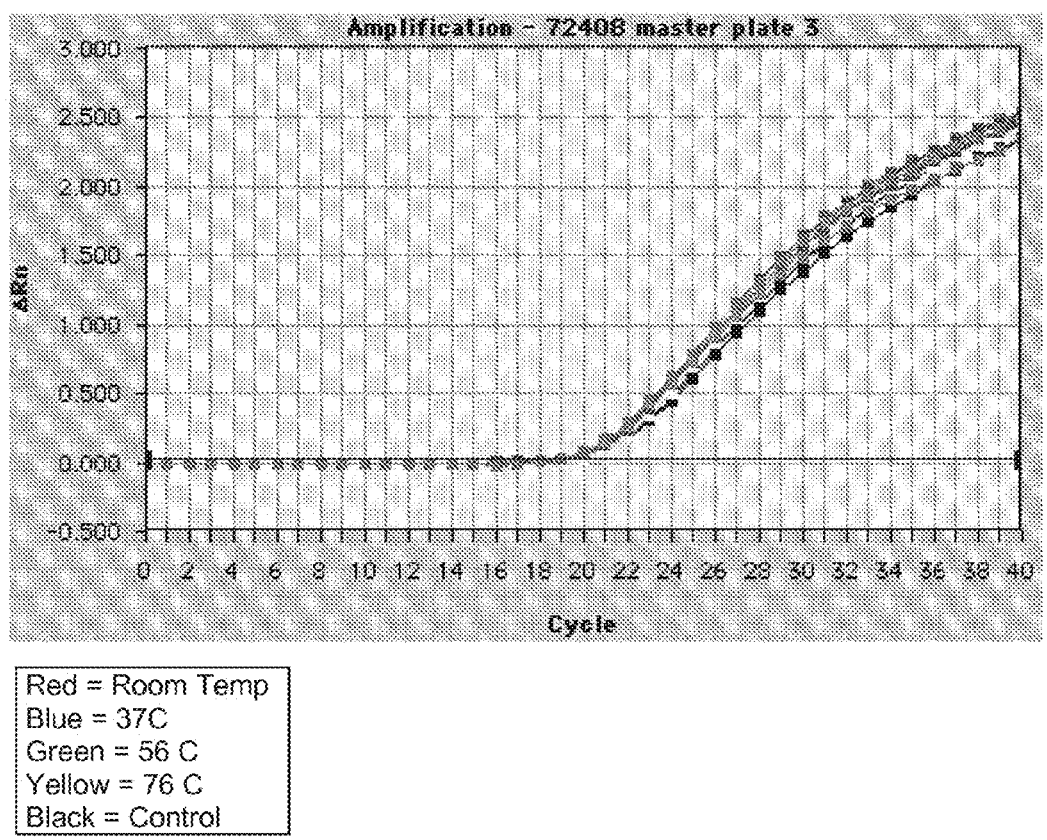
FIG. 3(b) shows real time PCR results for DNA recovered from 250 ng DNA samples following dry-state storage at room temperature, 37° C., 56° C., and 76° C., in a matrix composed of boric acid and histidine.

PCR reactions were carried out in a 25 µL volume. The reactions contained 1×ABI TaqMan buffer A, 3.5 mM MgCl2, 0.3 µM primers-probe, 0.2 mM dNTPs, and 0.125 µL of Amplitaq Gold at 5 U/µL. The conditions for these PCR tests were as follows: (1) 95° C. for 10 minutes; (2) 40 cycles of 95° C. for 15 seconds, 60° C. for 1 minute; and (3) 4° C. hold. Approximately 80 µg of DNA recovered from dry state storage (assuming 100% recovery) was used as template for each reaction. For controls, 80 µg of frozen DNA was used as template. All of PCR results were evaluated by real time PCR using ABI 7700. The results are shown in FIG. 3.

Example 8

Microarray Analysis of DNA Recovered from Dry-State Matrices

Microarray analysis was performed on DNA recovered from the dry-state matrices of Example 6. The DNA was recovered as described in Example 8. Affymetrix 6.0 and Illumina 1M Microarray SNP analyses were performed by Expression Analysis, Inc. (Durham, N.C.) as per manufacturer recommendations. The results of the analysis are shown in FIG. 4.

Example 9

Storage of Buccal Swab or Blood Swab Lysates in Dry-State Matrices Comprising Borax Whole blood or cheek cell samples are collected on cotton swabs and air dried. The swabs are later rehydrated by addition of 100 mM Borax in water, followed by heating to 95° C. for 10 minutes. The swab extract is collected from the swab by centrifugation or by squeezing the fluid from the swab by hand. The resulting solution is then aliquoted into one or more wells of a 96-well microtiter plate at a volume not to exceed about 200 µL per well. The plate is allowed to dry at room temperature, thus forming a dry-state matrix comprising biomolecules.

The biomolecules in the resulting dry-state matrix are recovered from a pre-selected well by the addition of a volume of water equal to the original fluid volume prior to drying (i.e., up to 200 µL/well). Recovered nucleic acid molecules are ready for use in applied genetic analyses or preparative nucleic acid biochemistry.

Example 10

Storage of Buccal Swab or Blood Swab Lysates in Dry-State Matrices Comprising Borax and Histidine Whole blood or cheek cell samples are collected on cotton swabs and air dried. The swabs are rehydrated by addition of 100 mM Borax and 2 mM-100 mM histidine in water, followed by heating to 95° C. for 10 minutes. The swab extract is collected from the swab by centrifugation or by squeezing the fluid from the swab by hand. The resulting solution is then aliquoted into one or more wells of a 96-well microtiter plate at a volume not to exceed about 200 µL per well. The plate is allowed to dry at room temperature, thus forming an inorganic storage matrix.

The biomolecules in the resulting dry-state matrix are recovered from a pre-selected well by the addition of a volume of water equal to the original fluid volume prior to drying (i.e., up to 200 µL/well). Recovered nucleic acid molecules are ready for use in applied genetic analyses or preparative nucleic acid biochemistry.

Example 11

RNA Stability During Dry-State Storage at Elevated Temperatures

Figure 5:
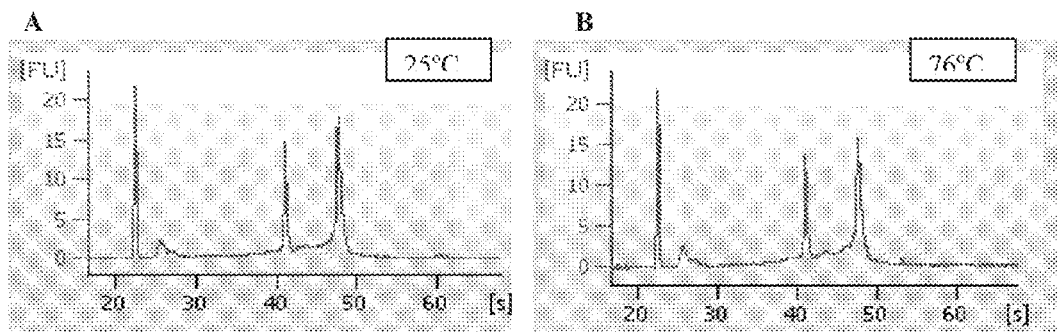
FIG. 5 is a set of graphs showing Agilent Bioanalyzer data for 1 microgram of purified total RNA following dry-state storage at (A) 25° C. or (B) 76° C. for 7 days in a matrix consisting of borate, citrate, EDTA, pyruvate, and dextran. The two peaks appearing at about 41 and about 48 seconds correspond to ribosomal RNA.
Figure 6:
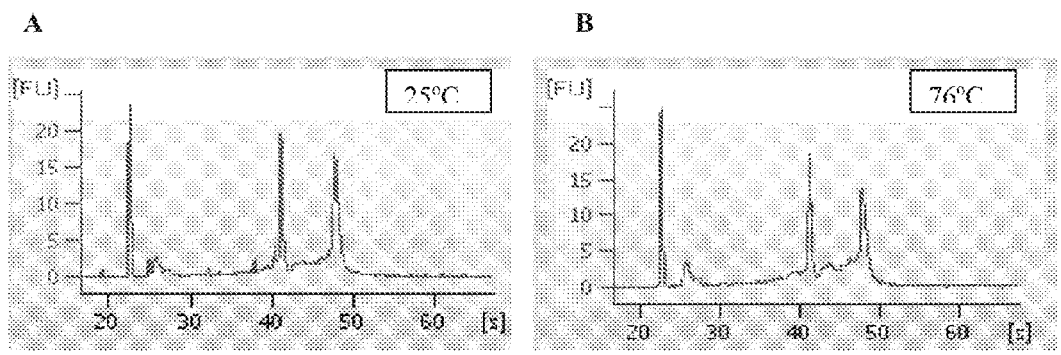
FIG. 6 is a set of graphs showing Agilent Bioanalyzer data for 1 microgram of purified total RNA following dry-state storage at (A) 25° C. or (B) 76° C. for 7 days in a matrix consisting of tris, borate, mannitol, and EDTA. The two peaks appearing at about 41 and about 48 seconds correspond to ribosomal RNA.
Figure 7:
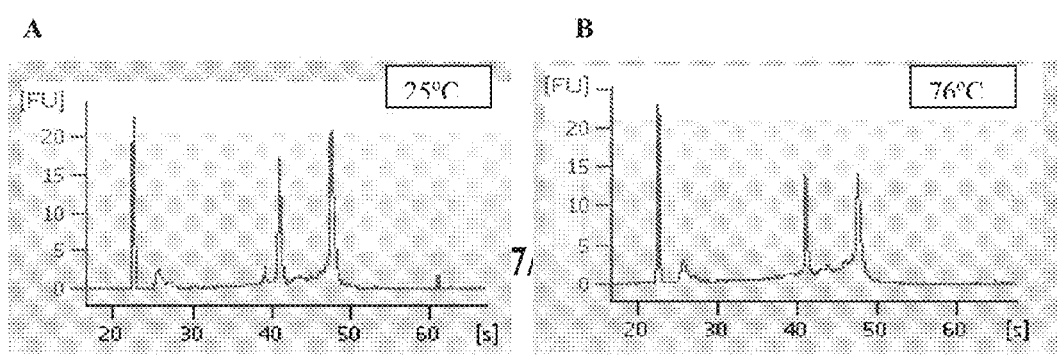
FIG. 7 is a set of graphs showing Agilent Bioanalyzer data for 1 microgram of purified total RNA following dry-state storage at (A) 25° C. or (B) 76° C. for 7 days in a matrix consisting of borate, citrate, mannitol, and dextran. The two peaks appearing at about 41 and about 48 seconds correspond to ribosomal RNA.
Figure 8:
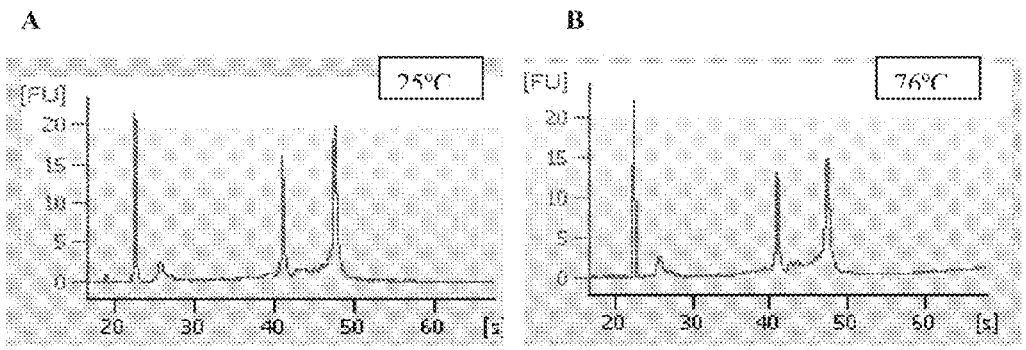
FIG. 8 is a set of graphs showing Agilent Bioanalyzer data for 1 microgram of purified total RNA following dry-state storage at (A) 25° C. or (B) 76° C. for 7 days in a matrix consisting of borate, citrate, mannitol, and pyruvate. The two peaks appearing at about 41 and about 48 seconds correspond to ribosomal RNA.
Figure 9:
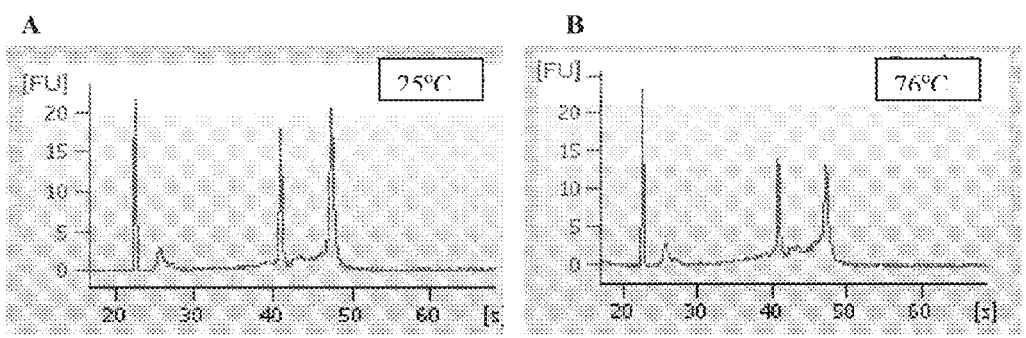
FIG. 9 is a set of graphs showing Agilent Bioanalyzer data for 1 microgram of purified total RNA following dry-state storage at (A) 25° C. or (B) 76° C. for 7 days in a matrix consisting of borate, citrate, pyruvate, and dextran. The two peaks appearing at about 41 and about 48 seconds correspond to ribosomal RNA.
Figure 10:
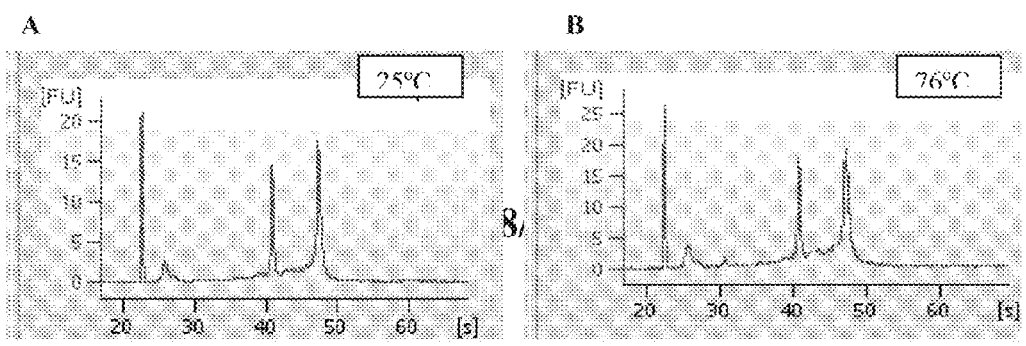
FIG. 10 is a set of graphs showing Agilent Bioanalyzer data for 1 microgram of purified total RNA following dry-state storage at (A) 25° C. or (B) 76° C. for 7 days in a matrix consisting of borate, citrate, EDTA, and dextran. The two peaks appearing at about 41 and about 48 seconds correspond to ribosomal RNA.
Figure 11:
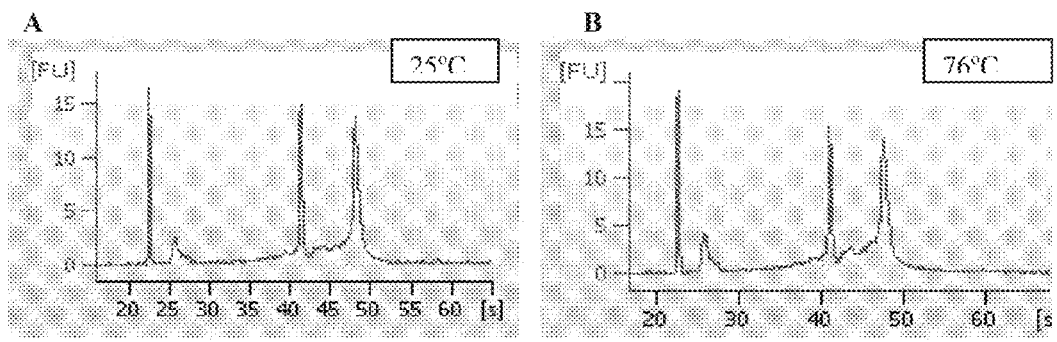
FIG. 11 is a set of graphs showing Agilent Bioanalyzer data for 1 microgram of purified total RNA following dry-state storage at (A) 25° C. or (B) 76° C. for 7 days in a matrix consisting of borate, EDTA, and pyruvate. The two peaks appearing at about 41 and about 48 seconds correspond to ribosomal RNA.
Figure 12:
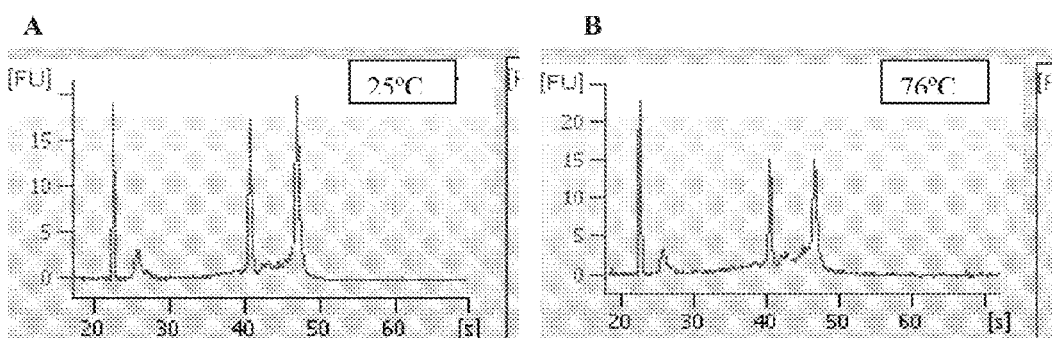
FIG. 12 is a set of graphs showing Agilent Bioanalyzer data for 1 microgram of purified total RNA following dry-state storage at (A) 25° C. or (B) 76° C. for 7 days in a matrix consisting of borate, citrate, and pyruvate. The two peaks appearing at about 41 and about 48 seconds correspond to ribosomal RNA.
Figure 13:
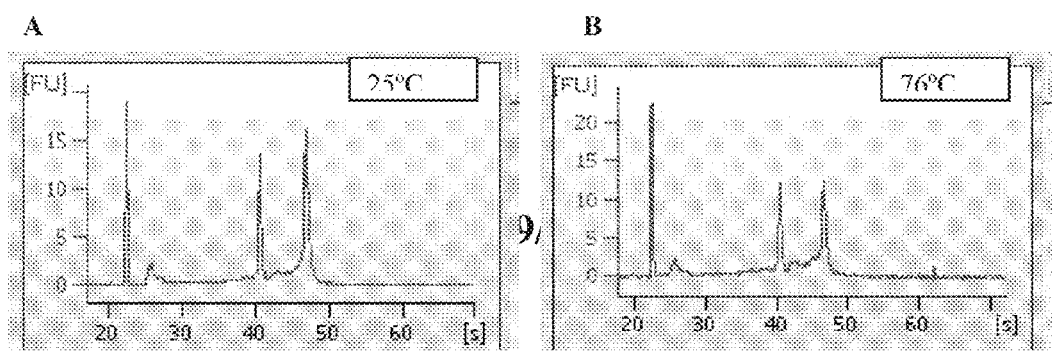
FIG. 13 is a set of graphs showing Agilent Bioanalyzer data for 1 microgram of purified total RNA following dry-state storage at (A) 25° C. or (B) 76° C. for 7 days in a matrix consisting of borate, citrate, and mannitol. The two peaks appearing at about 41 and about 48 seconds correspond to ribosomal RNA.
Figure 14:
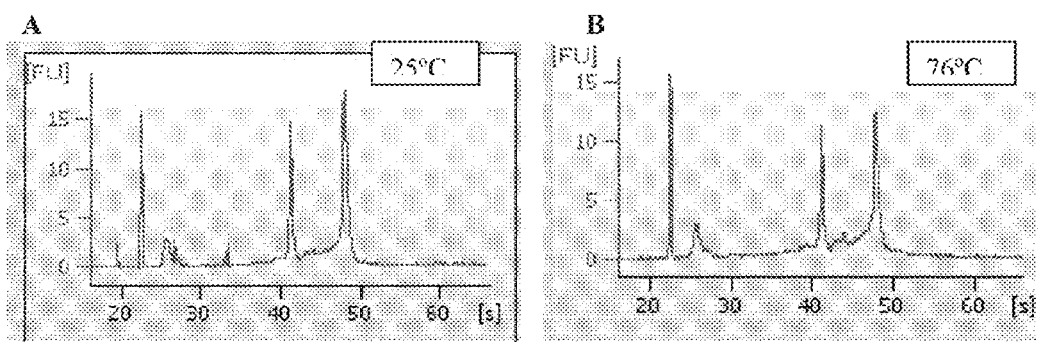
FIG. 14 is a set of graphs showing Agilent Bioanalyzer data for 1 microgram of purified total RNA following dry-state storage at (A) 25° C. or (B) 76° C. for 7 days in a matrix consisting of borate, citrate, and EDTA. The two peaks appearing at about 41 and about 48 seconds correspond to ribosomal RNA.
Figure 15:
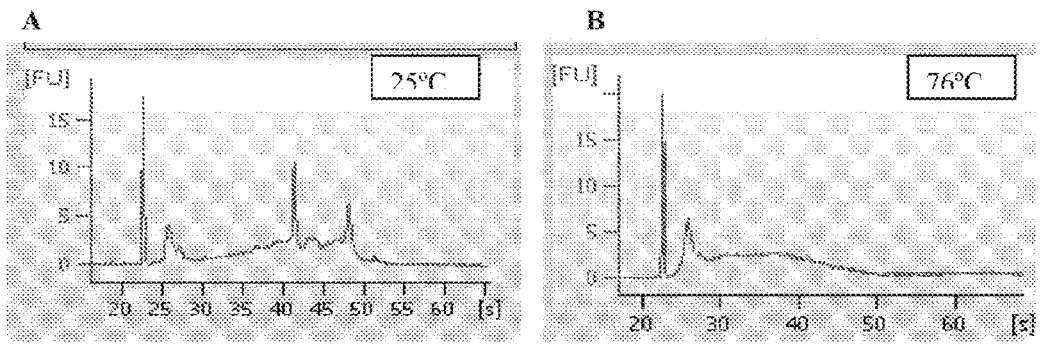
FIG. 15 is a set of graphs showing Agilent Bioanalyzer data for 1 microgram of purified total RNA following dry-state storage at (A) 25° C. or (B) 76° C. for 7 days in the absence of a matrix. The two peaks appearing at about 41 and about 48 seconds correspond to ribosomal RNA.

One microgram samples of purified total RNA were mixed with various compositions of the invention (as described below) and then stored in the dry state at (A) 25° C. or (B) 76° C. for 7 days. At that point, the samples were resuspended and analyzed on an Agilent Bioanalyzer. The dry-state matrices were as follows:
1) Borate, citrate, EDTA, pyruvate, and dextran (results shown in FIG. 5);
2) Tris, borate, mannitol, and EDTA (results shown in FIG. 6);
3) borate, citrate, mannitol, and dextran (results shown in FIG. 7);
4) borate citrate, mannitol, and pyruvate (results shown in FIG. 8);
5) borate, citrate, pyruvate, and dextran (results shown in FIG. 9);
6) borate, citrate, EDTA, and dextran (results shown in FIG. 10);
7) borate, EDTA, and pyruvate (results shown in FIG. 11);
8) borate, citrate, and pyruvate (results shown in FIG. 12);
9) borate, citrate, and mannitol (results shown in FIG. 13);
10) borate, citrate, and EDTA (results shown in FIG. 14);
11) no matrix control (results shown in FIG. 15).

In the Agilent bioanalyzer traces of total RNA, if the RNA is intact, the ribosomal RNA complement of the total RNA appears as a pair of sharp bands migrating at about 41 & 48 seconds. As the RNA degrades, strand breaks are incurred due to RNA backbone cleavage, thereby causing the sharp ribosomal RNA bands to be broadened, and eventually indetectible, as in FIG. 15(B).

Overall, the data in FIGS. 5-14 show that all ten of the compositions described above provide for high levels of RNA stabilization at 76° C., as assessed by the use of ribosomal RNA as a surrogate. This high temperature exceeds the maximum possible ambient shipping temperature predicted by FEDEX and the Dept. of Defense, thus indicating that the above 10 formulations (and other similar matrices), allow RNA to be stored and transported under extreme conditions in the dry state. By comparison, RNA stored dry in the absence of these compositions becomes moderately degraded when stored at 25° C. (FIG. 15(A)) and highly degraded when stored dry at 76° C. (FIG. 15(B)).

Additional compositions suitable for the dry-state storage, transport, and/or stabilization of RNA include: borate, citrate, mannitol, and dextran; borate, mannitol, pyruvate, and dextran; borate, EDTA, mannitol, pyruvate, and dextran; and borate, citrate, EDTA, mannitol, pyruvate, and dextran. For aqueous stabilization of RNA, one or more RNase inhibitors (e.g., as described herein) could be added to the compositions of this example.

All patents and publications, including all sequences disclosed within such patents and publications, referred to herein are expressly incorporated by reference.

Although the invention has been described with reference to the presently preferred embodiments and the foregoing non-limiting examples, it should be understood that various changes and modifications, as would be obvious to one skilled in the art, can be made without departing from the spirit of the invention. Accordingly, the invention is limited only by the following claims.

What is claimed is:

1. A dry-state matrix comprising:
   boric acid or a corresponding salt of boric acid; and
   a plasticizer and a hydroxyl radical scavenger, wherein histidine is the plasticizer and the hydroxyl radical scavenger;
   wherein the matrix is in a solid or dry form which can be converted to a liquid form by suspending, re-hydrating, or solubilizing the matrix in water.

2. The matrix of claim 1, further comprising a metal chelator.

3. The matrix of claim 1, wherein said matrix further comprises a singlet oxygen quencher selected from the group consisting of an alkyl imidazole, an indole, a sulfur-containing amino acid, a phenolic compound, an aromatic acid, azide, tocopherol, vitamin E derivatives, carotene, vitamin A derivatives, and any combination thereof.

4. The matrix of claim 1, wherein said matrix further comprises a metal chelator selected from the group consisting of EDTA, EGTA, o-phenanthroline, citrate, and any combination thereof.

5. The matrix of claim 1, wherein said matrix further comprises a hydroperoxide removing agent selected from the group consisting of catalase, pyruvate, glutathione, glutathione peroxidases, and any combination thereof.

6. The matrix of claim 1, Wherein said matrix is inert with respect to methods of nucleic acid amplification, nucleic acid digestion, and/or protein digestion.

7. The matrix of claim 1, further comprising a sample comprising biomolecules.

8. A method of storing biomolecules in a dry state, said method comprising:
   mixing a sample comprising biomolecules with a dry-state matrix of claim 1 to form a mixture, and
   drying said mixture to store said biomolecules in a dry state.

9. The method of claim 8, wherein said sample is a liquid sample, and wherein said liquid sample is mixed with said dry-state matrix.

10. The method of claim 8, wherein said biomolecules are stored at about 25° C. to about 72° C.

11. The dry-state matrix of claim 1, further comprising leucine.

12. The dry-state matrix of claim 11, further comprising a metal chelator.

13. The dry-state matrix of claim 12, wherein the metal chelator comprises EDTA.

14. The dry-state matrix of claim 13, wherein the metal chelator further comprises citrate.

15. The dry-state matrix of claim 1, wherein the dry-state matrix is paper free.

16. The dry-state matrix of claim 1, wherein the dry-state matrix is in a tube.

17. The dry-state matrix of claim 1, wherein the dry-state matrix is substantially free of cellulose.

18. The method of claim 8, wherein said dry-state matrix further comprises a metal chelator selected from the group consisting of EDTA, EGTA, o-phenanthroline, citrate, and any combination thereof.

19. The method of claim 8, wherein said dry-state matrix further comprises a hydroperoxide removing agent selected from the group consisting of catalase, pyruvate, glutathione, glutathione peroxidases, and any combination thereof.

20. The dry-state matrix of claim 1, wherein the matrix is substantially free of a biomolecule.

21. The dry-state matrix of claim 1, wherein the dry-state matrix is carried by a solid support.

22. The dry-state matrix of claim 21, wherein the solid support is selected from the group consisting of a cotton swab, a filter paper, or a sponge.

* * * * *